(12) United States Patent
Babcock et al.

(10) Patent No.: US 7,611,630 B2
(45) Date of Patent: Nov. 3, 2009

(54) METHOD AND DEVICE FOR EVALUATION OF PHARMACEUTICAL COMPOSITIONS

(75) Inventors: Walter Christian Babcock, Bend, OR (US); Dwayne Thomas Friesen, Bend, OR (US); Scott Baldwin McCray, Bend, OR (US)

(73) Assignee: Bend Research, Inc., Bend, OR (US)

( * ) Notice: Subject to any disclaimer, the term of this patent is extended or adjusted under 35 U.S.C. 154(b) by 391 days.

(21) Appl. No.: 10/590,989

(22) PCT Filed: Mar. 18, 2005

(86) PCT No.: PCT/IB2005/000711

§ 371 (c)(1), (2), (4) Date: Aug. 29, 2006

(87) PCT Pub. No.: WO2005/095950

PCT Pub. Date: Oct. 13, 2005

(65) Prior Publication Data

US 2007/0205155 A1  Sep. 6, 2007

Related U.S. Application Data

(60) Provisional application No. 60/557,897, filed on Mar. 30, 2004.

(51) Int. Cl.
*B01D 61/24* (2006.01)
*B01D 61/00* (2006.01)

(52) U.S. Cl. ............... 210/649; 210/321.6; 210/321.74; 210/634; 422/101; 436/809

(58) Field of Classification Search .................. None
See application file for complete search history.

(56) References Cited

U.S. PATENT DOCUMENTS 4,667,504 A    5/1987  Hobson
(Continued)

FOREIGN PATENT DOCUMENTS

| EP | 1 266 684 A1 | 9/2001 |
|----|--------------|--------|
| WO | WO 01/55698 A1 | 8/2001 |
| WO | WO 2004/037160 A2 | 5/2004 |

OTHER PUBLICATIONS

Zhu et al "A comparative study of artificial membrane permeability assay for high throughput profiling of drug absorption potential", Eur. J. Med. Chem. 37 (2002) 399-407.*
International Journal of Pharmaceutics, vol. 39, No. 1-2, 1987, pp. 59-74, XP002330920 ISSN: 0378-5173; Lee S Jet Al: "Ion-paired drug diffusion through polymer membranes" (abstract only).*

(Continued)

*Primary Examiner*—Krishnan S Menon
(74) *Attorney, Agent, or Firm*—Chernoff, Vilhauer, McClung & Stenzel, LLP

(57) ABSTRACT

A membrane-permeation test for evaluating pharmaceutical compositions is described. The method comprises the following steps: (1) providing a microporous membrane having a plurality of pores, the membrane having a feed side and a permeate side, wherein the feed side of the membrane is in fluid communication with the feed solution, and wherein the permeate side of the membrane is in fluid communication with a permeate solution; (2) administering a pharmaceutical composition to an aqueous solution to form a feed solution; and (3) measuring the concentration of drug in the permeate solution; wherein the feed side of the membrane is hydrophilic, and/or wherein the permeate solution comprises an organic fluid.

7 Claims, 6 Drawing Sheets

U.S. PATENT DOCUMENTS

| | | | |
|---|---|---|---|
| 4,681,858 | A | 7/1987 | Chaudhari et al. |
| 5,183,760 | A | 2/1993 | Sweetana et al. |
| 5,476,590 | A | 12/1995 | Brose et al. |
| 5,490,415 | A | 2/1996 | Mak et al. |
| 5,525,305 | A | 6/1996 | Minekus et al. |
| 5,962,250 | A | 10/1999 | Gavin et al. |
| 6,004,822 | A | 12/1999 | Li et al. |
| 6,022,733 | A | 2/2000 | Tam et al. |
| 6,043,027 | A | 3/2000 | Selick et al. |
| 6,271,038 | B1 | 8/2001 | Liu et al. |
| 6,294,134 | B1 | 9/2001 | Schenk et al. |
| 6,379,619 | B1 | 4/2002 | Rozga et al. |
| 6,569,686 | B2 | 5/2003 | Avdeef et al. |
| 7,468,281 | B2 * | 12/2008 | Kallury et al. ............ 436/178 |

OTHER PUBLICATIONS

W.I. Higuchi, "Effects of Interacting Colloids on Transport Rates," *Journal of Pharmaceutical Science*, 35:5(1964)532-535.

H. Takenaka, Y. Kawashim, and S.-Y. Lin, "Preparation of Enteric-Coated Microcapsules for Tableting by Spray-Drying Technique in In Vitro Simulation of Drug release from the tablet in GI Tract," *Journal of Pharmaceutical Science*, 69:12(1980)1388-1392.

G.E. Amidon, W.I. Higuchi, and N.F.H. Ho, "Theoretical and Experimental Studies of Transport of Micelle-Solubilized Solutes," *Journal of Pharmaceutical Science*, 71:1(1982)77-84.

F.L. Flynn, A.B. French, N.F.H. Ho, W.I. Higuchi, E.A. Ostafin, L.H. Warbasse, G.E. Amidon, and E. Williams, "Some Hydrodynamic boundary Layer Influences on Mass Transfer Coefficients," *Journal of Membrane Science*, 19(1984)289-308.

R. Neubert, "Transport Across Artificial Lipid Membranes. Part 24: Influence of Substance Properties on Diffusion Across Membranes," *Pharmazie*, 46(1991)442-444.

M. Kansy, F. Senner, and K. Gubernator, "Physiochemical High Throughput Screening: Parallel Artificial Membrane Permeation assay in the Description of Passive Absorption Processes," *Journal of Medicinal Chemistry*, 41:7(1998)1007-1010.

A. Avdeef, M. Strafford, E. Block, M.P. Balogh, W. Chambliss, and I. Khan, "Drug Absorption in Vitro Model: Filter-Immobilized Artificial Membranes. 2. Studies of the Permeability Properties of Lactones in Piper methysticum Forst," *European Journal Pharmaceutical Sciences*, 14(2001)271-280.

K. Sugano, H. Hamada, M. Machida, H. Ushio, K. Saitoh, and K. Terada, "Optimized Conditions of Bio-Mimetic Artificial Membrane Permeation Assay," *International Journal of Pharmaceutics*, 228(2001)181-188.

K. Sugano, H. Hamada, M. Machida, and H. Ushio, "High Throughput Prediction of Oral Absorption: Improvement of the Composition of the Lipid Solution Used in Parallel Artificial Membrane Permeation Assay," *Journal of Biomolecular Screening*, 6:3(2001)189-196.

F. Wohnsland and B. Faller, "High-Throughput Permeability pH Profile and High-Throughput Alkane/Water log P with Artificial Membranes," *Journal Medicinal Chemistry*, 44(2001)923-930.

E.H. Kerns, "High Throughput Physiochemical Profiling for Drug Discovery," *Journal of Pharmaceutical Science*, 90:11(2001)1838-1858.

I.J. Hidalgo, "Assessing the Absorption of New Pharmaceuticals," *Current Topics in Medicinal Chemistry*, 1(2001)385-41.

G.S.J. Mannens, H. Bohets, P. Verboven, K. Steemans, K. Lavrijsen, and W. Meuldermans, "3. Rapid Permeability Screening in Drug Discovery to Predict Human Intestinal Absorption," from Ernest Schering Research Foundation Workshop, vol. 37, 2002, pp. 49-67.

C. Lohmann, S. Huwel, and H.-J. Galla, "Predicting Blood-Brain Barrier Permeability of Drugs: Evaluation of Different In Vitro Assays," *Journal of Drug Targeting*, 10:4(2002)263-276.

K. Sugano, N. Takata, M. Machida, K. Saitoh, and K. Terada, "Prediction of Passive Intestinal Absorption Using Bio-Mimetic Artificial Membrane Permeation Assay and the Paracellular Pathway Model," *International Journal of Pharmaceutics*, 241(2002)241-251.

C. Zhu, L. Jiang, G.-M. Chen, and K.-K. Hwang, "A Comparative Study of Artificial Membrane Permeability assay for High Throughput Profiling of Drug Absorption Potential," *European Journal of Medicinal Chemistry*, 37(2002)399-407.

S.J. Lee, T. Kurihara-Bergstrom, and S.W. Kim, "Ion-Paired Drug Diffusion Through Polymer Membranes," *International Journal of Pharmaceutics*, 47(1987)59-73.

* cited by examiner

METHOD AND DEVICE FOR EVALUATION OF PHARMACEUTICAL COMPOSITIONS

This is a 371 of PCT/IB2005/000711 filed Mar. 18, 2005 and claims priority of U.S. Ser. No. 60/557,897 filed Mar. 30, 2004.

FIELD OF THE INVENTION

This invention relates to an in vitro method that can be used to evaluate pharmaceutical compositions, and a device for performing such tests.

BACKGROUND OF THE INVENTION

The pharmaceutical industry uses a wide variety of tests to evaluate active pharmaceutical ingredients and pharmaceutical compositions. These tests are used to characterize the performance of the candidates and/or compositions over a wide range of conditions. Ideally, such tests predict the in vivo performance of the candidate or composition, thus minimizing the number of in vivo tests needed to evaluate and select candidates, reducing development time and costs.

Much of the prior art is focused on estimating the intrinsic in vivo permeability of drugs through the epithelial membrane in the GI tract from in vitro test data. Several of these in vitro tests utilize a membrane to aid in predicting in vivo performance. The state of the art is summarized in many articles, including, for example, "Assessing the Absorption of New Pharmaceuticals," by Hidalgo in *Current Topics in Medicinal Chemistry*, 2001, 1, 385-401, and "High Throughput Physicochemical Profiling for Drug Discovery," *J. Pharm Sci.*, 2001, 90(11), 1838-1858.

Several of these in vitro membrane-based tests utilize cultured cell lines, including Caco-2, HT-29, and MDCK cells. Examples of devices for performing such tests are described in U.S. Pat. Nos. 5,962,250, 6,022,733, and 6,043,027. However, such methods are time consuming, expensive, and often give widely varying results. In addition, such tests are generally designed for estimating the intrinsic permeability of individual compounds through the epithelial membrane. While effective for this, they are not always effective for evaluating the rate of absorption for pharmaceutical compositions.

Other tests utilize artificial or synthetic membranes to estimate the in vivo absorption and intrinsic permeability of individual compounds. These tests include immobilized artificial membrane (IAM) columns, the parallel artificial membrane permeation assay (PAMPA), and filter-immobilized artificial membranes. Methods and equipment for performing such tests are disclosed in numerous literature references, including Kansy et al., *J. Med. Chem.*, 1998, 41, 1007-1010; Wohnsland and Faller, *J. Med. Chem.*, 2001, 44, 923-930; Sugano et al., *Intl. J. Pharmaceutics*, 228 (2001) 181-188; Sugano et al., *J. Biomolecular Screening*, 6(3) (2001) 189-196; Sugano et al., *Intl. J. Pharmaceutics*, 241 (2002) 241-251; Zhu et al., *Eur. J. Med. Chem.*, 37 (2002) 399-407; Avdeef et al., *Eur. J. Pharm. Sci.*, 14 (2001) 271-280.

While the prior-art methods and devices may be suitable for estimating the intrinsic permeability of individual compounds in vivo, the inventors have discovered that they have significant limitations. Generally, the methods are not suitable for evaluating low-solubility drugs. In addition, the methods often do not adequately predict the rate of absorption of drugs from pharmaceutical compositions. In the prior-art test methods and devices, the permeate side of the membrane contains a solution (sometimes referred to as the acceptor solution in the art) similar to that used on the feed side (sometimes referred to as the donor solution in the art), while the membrane contains an organic or lipid solution, sometimes in the form of a bilayer membrane. In such cases, the permeate solution does not act as a sink for the drug, severely limiting the driving force for transport across the membrane, especially for low solubility drugs. While additives have been added to the permeate solution to improve the solubility of the drug therein, such additives do not work for all drugs and can destabilize the membrane. In addition, the prior art methods do not correlate well with in vivo results, especially for drugs that partition into bile salt or lecithin micelles present in vivo, nor do they correlate well with solubilized drug forms.

Thus, there is a continuing need in the art to develop effective and efficient methods for estimating the in vivo absorption rate for drugs present in pharmaceutical compositions.

SUMMARY OF THE INVENTION

To overcome the limitations of the prior art, the inventors developed an in vitro membrane-permeation test to evaluate the performance of drug compositions under conditions that mimic in vivo conditions. In one aspect, the invention provides a method for evaluating a pharmaceutical composition. The method comprises the following steps: (1) providing a microporous membrane having a plurality of pores, the membrane having a feed side and a permeate side, wherein the feed side of the membrane is in fluid communication with a feed solution, and wherein the permeate side of the membrane is in fluid communication with a permeate solution; (2) administering a pharmaceutical composition to an aqueous solution to form the feed solution; and (3) measuring the concentration of drug in the permeate solution, wherein the feed side of the membrane is hydrophilic.

In another aspect, the invention provides a method for evaluating a pharmaceutical composition. The method comprises the following steps: (1) providing a microporous membrane having a plurality of pores, the membrane having a feed side and a permeate side, wherein the feed side of the membrane is in fluid communication with a feed solution, and wherein the permeate side of the membrane is in fluid communication with a permeate solution; (2) administering a pharmaceutical composition to an aqueous solution to form the feed solution; and (3) measuring the concentration of drug in the permeate solution, wherein the permeate solution comprises an organic fluid.

In yet another aspect, the invention provides a device for evaluating pharmaceutical compositions. The device comprises (1) a feed reservoir for containing a feed solution, (2) a permeate reservoir for containing a permeate solution, and (3) a microporous membrane having a plurality of pores, the membrane having a feed side and a permeate side, the membrane separating the feed reservoir and the permeate reservoir, and wherein the feed side of the membrane is hydrophilic.

In still another aspect, the invention provides a multi-well plate for evaluating a pharmaceutical composition. The multi-well plate comprises (1) a filter plate, and (2) an acceptor plate, wherein the filter plate has a plurality of filter wells, and the acceptor plate has a plurality of acceptor wells, and wherein the bottom of each of the filter wells comprises a microporous membrane having a plurality of pores, the membrane having a feed side and a permeate side, wherein the feed side of the microporous membrane is hydrophilic. The feed side of the membrane may be contacted with a feed solution while simultaneously, the permeate side of said membrane may be contacted with a permeate solution.

The inventors have discovered that low-solubility drugs may be formulated into compositions that, when added to an aqueous solution such as gastrointestinal (GI) fluids, are capable of providing high-energy species of drug that have a higher free energy than dissolved drug. In vivo, these high-energy species may replenish the dissolved drug in solution as it is absorbed by transport across the epithelial lipid membrane, resulting in further drug absorption. Conventional in vitro dissolution tests often fail to measure the contribution of such high-energy species to in vivo performance.

The method and device of the present invention can be used to evaluate (1) the dissolved-drug concentration provided by a composition in solution, (2) the effect of high-energy drug species present in the feed on permeation through the unstirred boundary layer adjacent to the membrane, and (3) the capability of high-energy species to replenish dissolved drug as drug is removed through the membrane. Without wishing to be bound by any theory or mechanism of action, it is believed that the method of the present invention provides a more accurate assessment of the in vivo performance of a pharmaceutical composition than the in vitro tests currently employed in the art. In addition, the method of the present invention allows the rapid evaluation of a large number of pharmaceutical compositions in a cost effective manner, and can be used in high throughput screening (HTS) applications.

The foregoing and other objectives, features, and advantages of the invention will be more readily understood upon consideration of the following detailed description of the invention, taken in conjunction with the accompanying drawings.

DETAILED DESCRIPTION OF THE PREFERRED EMBODIMENTS

Figure 1:
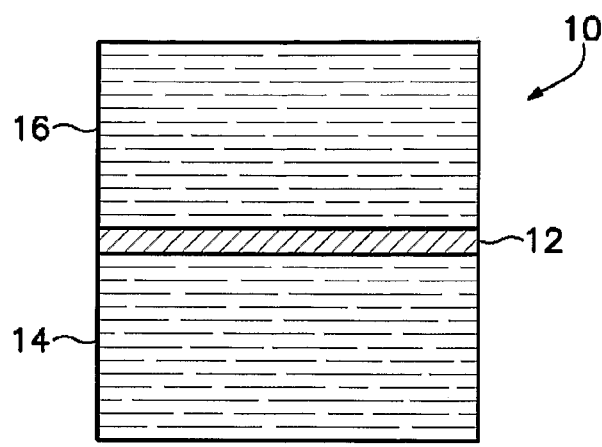
FIG. 1 schematically shows a cross section of an exemplary membrane-permeation test system.

The inventors designed the in vitro membrane-permeation test to overcome the limitations of the prior art and to provide information that can be utilized to better predict drug absorption in vivo and allow differentiation and selection of formulations with improved rates and extents of drug absorption. The inventive in vitro membrane-permeation test utilizes a water-immiscible organic fluid held in the pores of a microporous film that allows drug to partition therein, mimicking how drug partitions into and permeates the epithelial lipid membrane of the intestinal wall. The water-immiscible organic fluid not only fills the membrane pores, but also acts as the permeate solution; the relatively high partition coefficient of the drug for the organic fluid relative to the aqueous feed allows the permeate to act as a sink for the drug such that, at equilibrium, most of the drug is in the permeate solution. In addition, the water-immiscible organic fluid has a very low solubility in water, which is important for maintaining a well-defined interface between the aqueous and organic phases. Additionally, the organic fluid has a low volatility, which is important for stable and safe operation of the test. Suitable materials for use as the organic fluid are described herein.

The test also mimics the so-called "unstirred water layer" that is next to the epithelial lipid membrane, which affects the rate of transport of dissolved drug, drug in bile-salt micelles, and high-energy drug species through the lipid membrane. This "unstirred water layer" that exists in vivo is composed of a layer of mucus and mucin that coats the epithelial cells of the intestinal wall. For most lipophilic drugs with low aqueous solubility, diffusion through this unstirred mucus/mucin layer is one of the major resistances to drug absorption. To mimic this unstirred water layer in the membrane-permeation test, a thin layer of pores on the feed side of the microporous membrane are made sufficiently hydrophilic that they become filled with the aqueous feed solution during the test, providing a well-defined, unstirred water layer in the surface pores of the membrane.

Without wishing to be bound by any particular theory, it is believed that when a pharmaceutical composition is introduced to an aqueous use environment such as the GI tract, the drug in the aqueous environment may be present in various species that can affect the rate of absorption through the epithelial lipid membrane. The inventors believe that at least four different drug-containing species may be formed: (1) dissolved drug; (2) drug present within bile salt micelles that are naturally occurring in the GI tract (see, for example, Amidon et al., *J. Pharm. Sci.*, 71, 77-84, 1982; and Higuchi, *J. Pharm. Sci.*, 53, 532-535, 1964); (3) drug present in sub-micron, high-energy drug species; and (4) precipitate or other drug-containing solids that are relatively large. As used herein, the term "dissolved drug" refers to drug molecules which are dissolved in the aqueous solution and are generally either monomeric or clusters of no more than about 100 molecules. As used herein, "dissolved neutral drug" refers to either (1) dissolved drug for a drug that is not ionizable, or (2) the dissolved neutral, unionized form of a drug that is ionizable. As used herein, "dissolved ionized drug" refers to the dissolved, ionized species of a drug that is ionizable. As used herein, the term "drug present within bile salt micelles" refers to drug molecules that are associated with lipophilic species that occur naturally in the GI tract. These species tend to be small and are either dissolved or suspended in the aqueous environment of the GI tract. Examples of such species include bile-salt micelles, fat emulsions, and proteins. As used herein, the term "high-energy drug species" refers to drug molecules that are physically associated with excipients present in the pharmaceutical composition but remain small and thus, remain suspended in solution. Examples of such high-energy drug species include drug-containing aggregates, colloids, polymer/drug assemblies, or drug adsorbed to small solid substrates. "Precipitate" is a general term for any relatively large particulates that form and fall out of solution, either naturally or upon centrifugation. Such precipitate may comprise one or more or all of the following forms: (1) crystalline drug; (2) amorphous drug; (3) drug adsorbed to or associated with other species present in the pharmaceutical composition; and/or (4) drug adsorbed to or associated with species that occur naturally in the GI tract. Precipitate generally has a sufficient density and size so as to drop out of solution (typically greater than about 5 to 10 microns in average diameter).

Each of these drug-containing species can affect the rate of absorption of drug in vivo. The membrane-permeation test allows for evaluation of feed solutions containing any or all of these species. For example, feed solutions containing various concentrations of bile salt micelles (to simulate fasted and/or fed conditions) may be employed. Suitable apparatus for performing the test of the present invention, the method of performing the test, suitable membranes and organic fluids, and pharmaceutical formulations suitable for evaluation in the inventive test are described below.

Apparatus for Performing the Test

Figure 2:
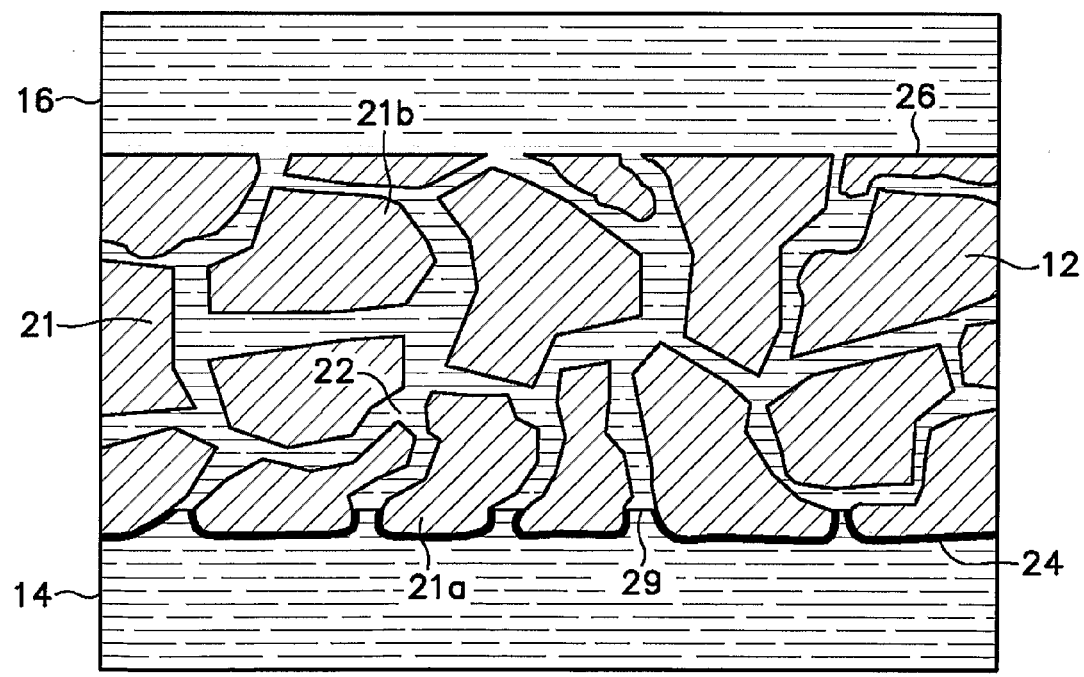
FIG. 2 schematically shows a cross section of an exemplary microporous membrane used in the membrane-permeation test.

Turning now to the drawings, wherein the same numerals indicate like elements, FIG. 1 shows schematically a cross section of an exemplary membrane-permeation test system 10. The system consists of a microporous membrane 12 that separates a feed solution 14 from an organic fluid 16. FIG. 2 shows schematically a cross section of the details of the microporous membrane 12. As shown schematically in FIG. 2, the microporous membrane has a feed side 24 and a permeate side 26, with the feed side 24 in fluid communication with the feed solution 14 and the permeate side 26 in fluid communication with the organic fluid 16. The microporous membrane 12 has a plurality of internal walls 21, which each define respective pores 22. The feed side 24 of the microporous membrane 12 has a hydrophilic portion 21a. As shown schematically in FIG. 2, the feed-side portion 21a of the internal wall 21 that is proximate to the feed side 24 of the microporous membrane 12 is hydrophilic. The permeate-side portion 21b of the internal wall 21 is hydrophobic. In use, the feed-side portion 21a of the pores 22 of the microporous membrane 12 that are hydrophilic are filled with feed solution 14, while the permeate-side portion 21b are filled with organic fluid 16. Thus, the boundary 29 between the aqueous feed solution 14 and the organic permeate solution 16 is located within the pores 22. Note that the pores 22 of the microporous membrane 12 in FIG. 2 are shown in two dimensions for illustration purposes. In actual microporous membranes the pores are often interconnected and are tortuous, taking on a "foam" or "sponge-like" structure. The rendering shown in FIG. 2 is not intended to be limiting.

Figure 3:
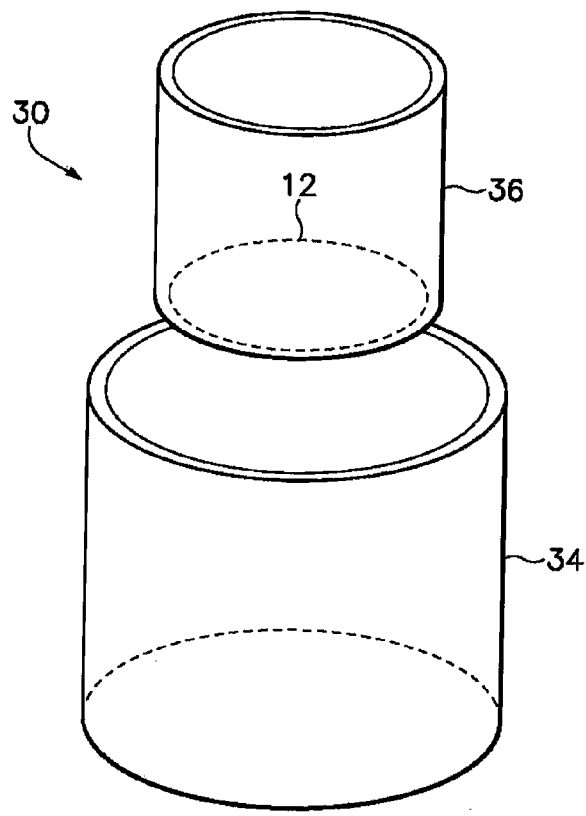
FIG. 3 schematically shows an assembly view of an exemplary device useful for performing the method of the present invention.

The membrane-permeation test of the present invention may be performed in any apparatus that allows (1) the feed solution to be placed in contact with the feed side of the microporous membrane described herein; and (2) the permeate solution to be placed in contact with the permeate side of the microporous membrane as described herein. FIG. 3 shows schematically an exploded view of an exemplary device 30 for performing the method of the present invention. The device comprises a microporous membrane 12 attached to a permeate reservoir 36 such that the permeate side of the microporous membrane is facing the permeate reservoir 36 and the feed side of the microporous membrane is facing the feed reservoir 34. The permeate reservoir contains the permeate solution, while the feed reservoir contains the feed solution. In use, the permeate reservoir 36 is located within the feed reservoir 34.

The permeate reservoir may be made from any suitable material that can withstand continuous exposure to the organic fluid. Examples of suitable materials include ceramics, such as glass; metals, such as stainless steel, copper, and brass; and polymers, such as polypropylene, polyethylene, polystyrene, polycarbonate, acrylic, and polytetrafluoroethylene (PTFE). The feed reservoir may also be made from any suitable material, such as those described above for the permeate reservoir.

In one embodiment, the microporous membrane is attached to the permeate reservoir. As used herein, the term "attached" means that the membrane is sealed, fixed or otherwise in contact with the permeate reservoir, thus preventing permeation of materials from the feed solution to the permeate solution or visa versa other than through the membrane. The membrane may be attached to the permeate reservoir through the use of procedures well known in the art, such as by gluing the membrane to the permeate reservoir with an appropriate adhesive, by using a clamping system with or without O rings to effect the seal, and by melt-sealing the membrane to the permeate reservoir.

In an alternative embodiment, not shown in the figures, the microporous membrane may be attached to the feed reservoir. In yet another embodiment, the microporous membrane may be attached to both the feed reservoir and the permeate reservoir.

Figure 4:
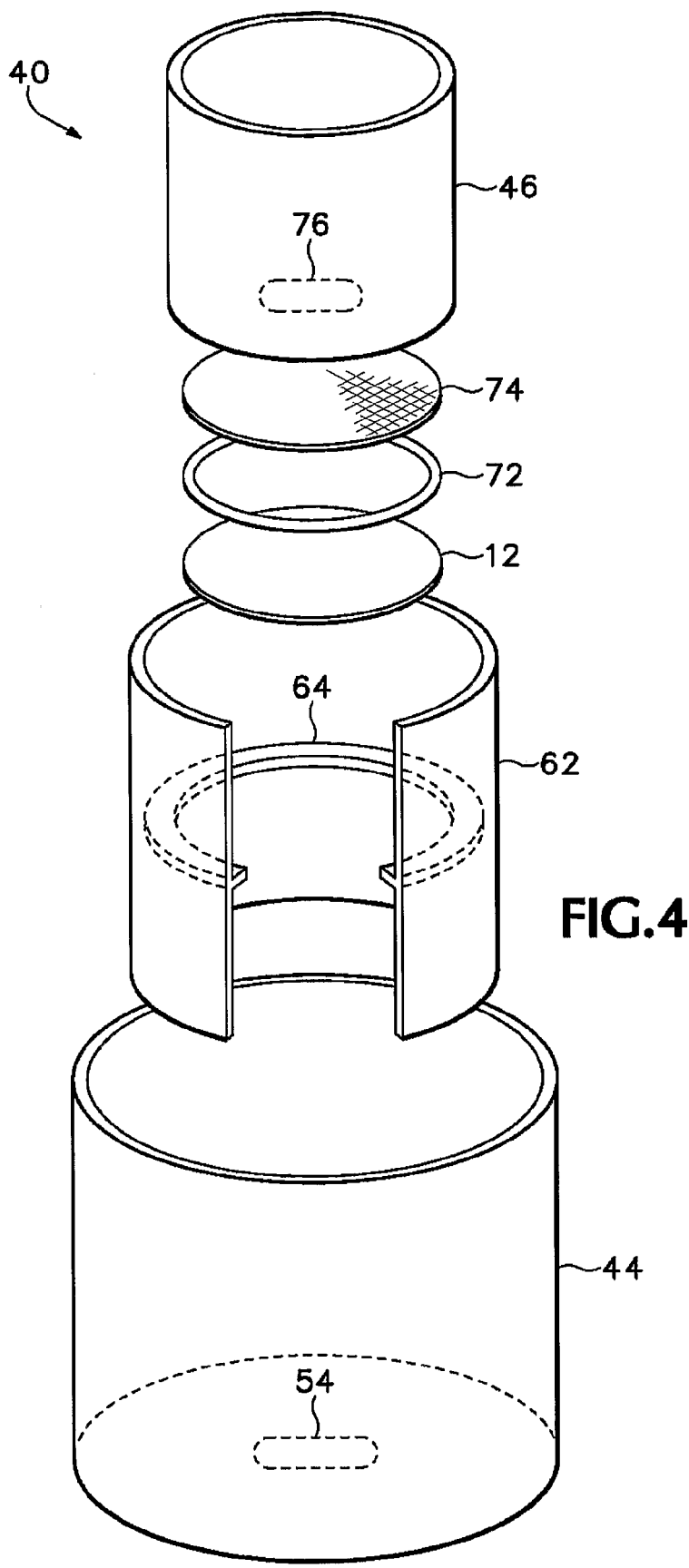
FIG. 4 schematically shows an assembly view of an exemplary device useful for performing the method of the present invention.

FIG. 4 shows schematically an assembly view of an exemplary device 40 for performing the method of the present invention. The device comprises a microporous membrane 12 attached to a permeate reservoir 46 such that the permeate side of the microporous membrane is facing the permeate reservoir 46 and the feed side of the microporous membrane is facing the feed reservoir 44. Feed reservoir 44 contains a feed stir bar 54 used to mix the feed solution. The permeate reservoir 46 includes an O-ring 72 located adjacent to the permeate side of the microporous membrane 12; a screen 74 located adjacent to the O-ring 72; and a stir bar 76 that sits on top of the screen 74. The screen 74 prevents the stir bar 76 from directly contacting the permeate-side of the microporous membrane 12 during operation. The O-ring 72 acts as a spacer between the screen 74 and the permeate side of the microporous membrane 12. In use, the permeate reservoir 46 is placed into a reservoir holder 62, the holder including a stop 64 that allows the permeate reservoir 46 to be placed at a reproducible and constant height above the bottom of the feed reservoir 44 and the feed stir bar 54.

Figure 5:
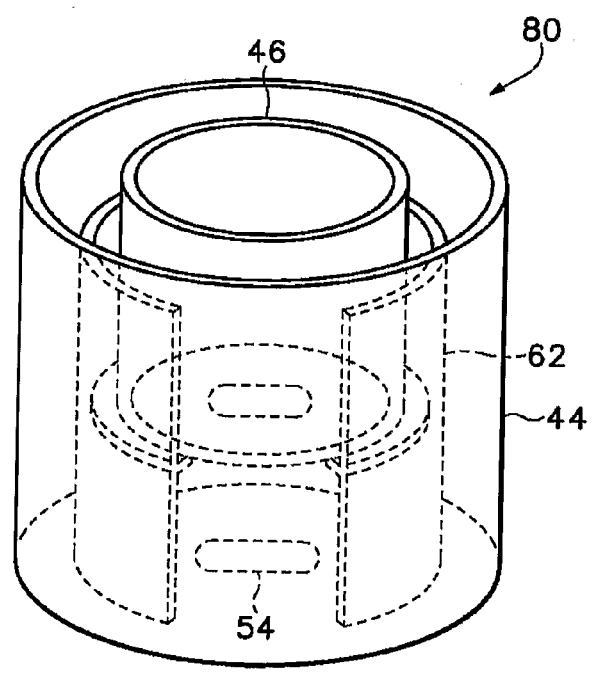
FIG. 5 schematically shows a cross section of the device shown in FIG. 4.

FIG. 5 shows schematically an assembled view 80 of the device 40 shown in FIG. 4. When assembled, permeate reservoir 46 fits into the reservoir holder 62. The permeate reservoir 46 in reservoir holder 62 is then placed inside the feed reservoir 44 such that the feed stir bar 54 is approximately centered under the permeate reservoir 46.

In another embodiment, not shown in the drawings, the membrane is attached to the feed reservoir, which then is placed inside the permeate reservoir. In yet another embodiment not shown, the feed reservoir and permeate reservoir are placed next to each other, with the membrane placed between the two reservoirs.

In a preferred embodiment, the reservoir holder and feed reservoir are designed to minimize the volume of feed solution required to perform the test. It is also desirable that the liquid height of the feed solution and the liquid height of the permeate solution are about the same during the test to minimize any hydrostatic pressure differences between the two solutions. In a preferred embodiment, the height of the feed solution is somewhat higher than that of the permeate solution to ensure that there is a small but positive pressure difference between the feed solution and the permeate solution; that is, the feed pressure exerted on any point of the membrane is greater than the permeate pressure exerted on the opposite side of the membrane. This ensures that the permeate solution does not flow through the membrane pores into the feed solution and also ensures that the surface of the feed side of the microporous membrane is wetted by the feed solution and the feed solution/organic fluid interface is located within the pores on the feed side of the membrane.

Figure 6:
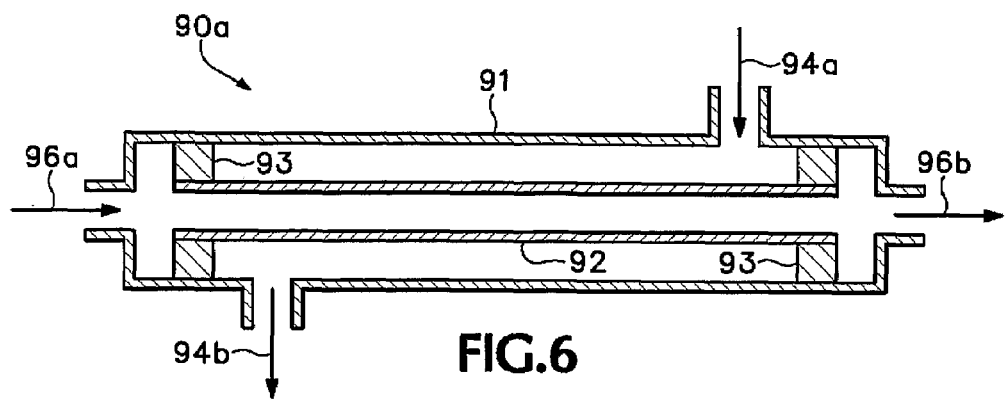
FIG. 6 schematically shows a cross section view of an exemplary device useful for performing the method of the present invention that utilizes a hollow-fiber or tubular microporous membrane.
Figure 7:
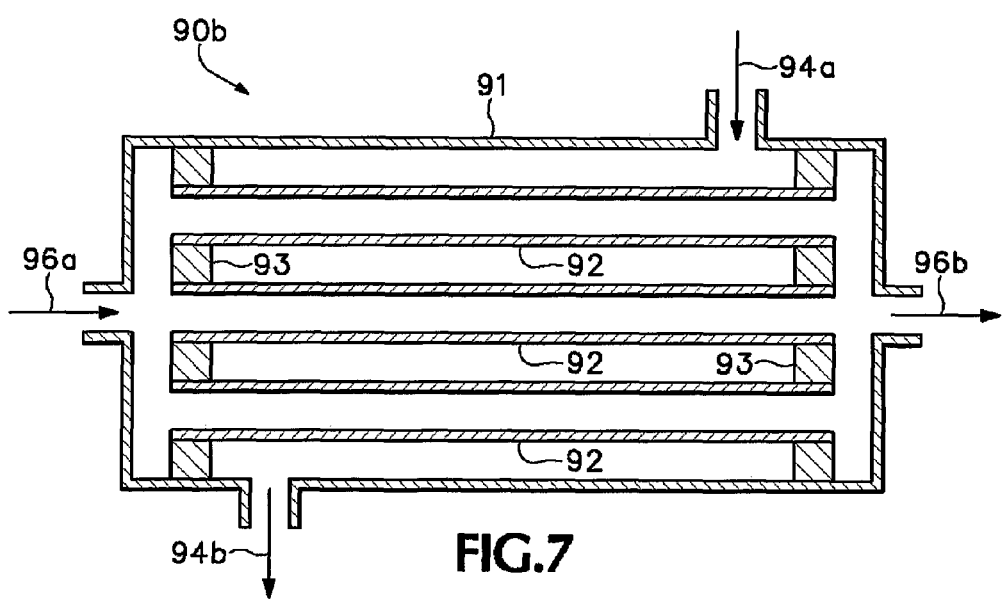
FIG. 7 schematically shows a cross section view of an exemplary device useful for performing the method of the present invention that utilizes a plurality of hollow-fiber or tubular microporous membranes.

In yet another embodiment, the microporous membrane is in the form of a hollow fiber or tube. FIG. 6 shows schematically a cross section view of an exemplary device 90*a* of the present invention that utilizes a hollow-fiber or tubular microporous membrane. FIG. 7 shows schematically a cross section view of an exemplary device 90*b* of the present invention that utilizes a plurality of hollow-fiber or tubular microporous membranes. In FIG. 6, the hollow fiber or tube 92 is sealed into a housing 91 using a potting material 93. The inside diameter of the fiber or tube may range from about 50 μm to about 4 cm, preferably about 400 μm to about 2 cm, more preferably about 600 μm to about 2 cm. Generally, larger diameter fibers or tubes are preferred to minimize the pressure drop incurred when solution flows therethrough. In one embodiment, the feed side of the membrane is on the outside surface of the hollow fiber or tube, while the permeate side of the membrane is on the inside surface. As with flat microporous membrane, the feed side of the hollow-fiber or tube is hydrophilic. In such cases, feed solution 94*a* is directed on the outside of the hollow fiber or tube, exiting the housing at 94*b*. The permeate solution 96*a* is directed down the inside of the hollow-fiber or tube, and exits the other end of the hollow-fiber or tube 96*b*. Alternatively, the feed side of the membrane may be the inside surface of the hollow fiber or tube, while the permeate side is the outside surface of the hollow fiber or tube. In such cases, the feed solution is directed down the inside of the hollow fiber or tube, while the permeate solution is directed down the outside of the hollow fiber or tube.

During operation, it is preferred that the feed solution and permeate solution be stirred or mixed. In the embodiments shown in FIG. 4 and FIG. 5, the device uses a stir bar in the feed solution and in the permeate solution. Such stir bars may be driven by magnetic, mechanical, or other means known in the art. Alternatively, other means for stirring or mixing the feed solution and permeate solution may be utilized, including mechanical mixers such as overhead mixers, vibrating tables, oscillating tables, or sonicators. In another embodiment, the feed solution and/or permeate solution may be circulated past the microporous membrane using a pump or other means for circulating fluid. Such pumped systems have an advantage when using flow-through cells for measurement of the concentration of drug in the permeate solution. Pumped systems are also preferred for devices that use hollow fiber or tubular microporous membranes.

Figure 8:
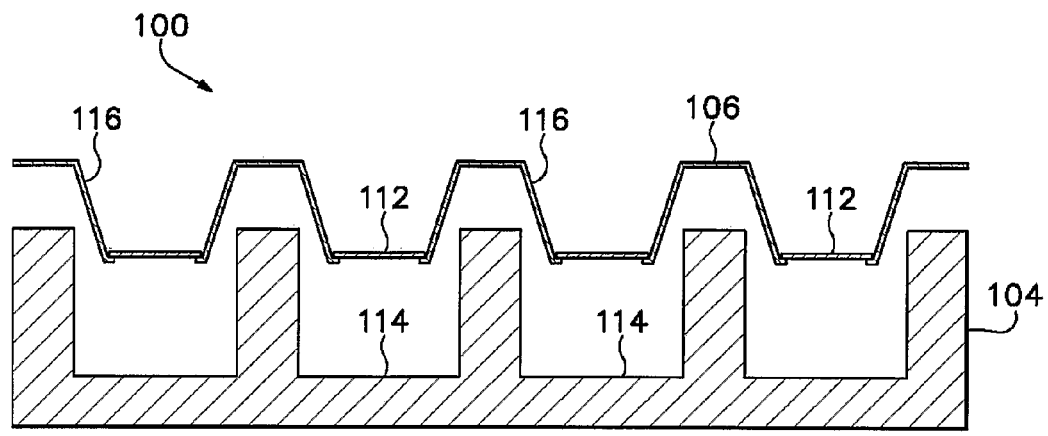
FIG. 8 schematically shows a cross section of an exemplary multi-well plate suitable for performing the method of the present invention.
Figure 9:
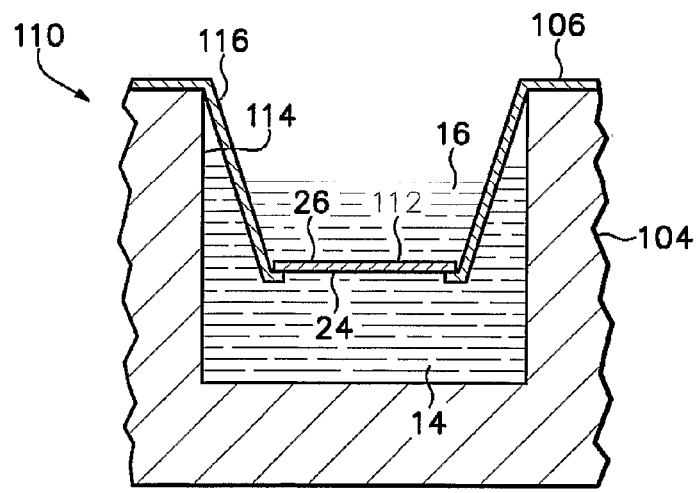
FIG. 9 schematically shows a cross section of a single well of an exemplary multi-well plate suitable for performing the method of the present invention.

The method of the present invention may also be performed in a multi-well format, such as in 6-well, 24-well, 96-well, and 384-well plates similar in shape to those well known in the art. FIG. 8 shows schematically a cross section of four representative wells of an exemplary multi-well plate 100 suitable for performing the method of the present invention, while FIG. 9 shows a cross section of a single well of an exemplary multi-well plate 110. The device comprises an "acceptor plate" 104 and a "filter plate" 106. The filter plate 106 has a plurality of filter wells 116. A microporous membrane 112 forms the bottom of the filter well 116 in the filter plate 106. The acceptor plate 104 has acceptor wells 114. The device is designed such that the filter wells 116 in the filter plate 106 fit into the acceptor wells 114 of the acceptor plate 104. When used in the method of the present invention, the feed solution 14 may be placed into the acceptor wells 114 of the acceptor plate. In such cases, the bottom surface 24 of the microporous membrane 112 (that is, the surface facing the acceptor plate 104) is hydrophilic. The organic fluid 16 is placed in the filter wells 116 of the filter plate 106. Thus, when the filter plate 106 is placed onto the acceptor plate 104, the feed solution 14 is in fluid communication with the bottom side 24 (that is, the feed side) of the microporous membrane 112, while the permeate solution 16 (that is, the organic fluid) is in fluid communication with the top side 26 (that is, the permeate side) of the microporous membrane 112. Preferably, the height of the feed solution 14 is somewhat higher than that of the permeate solution 16 to ensure that there is a small but positive pressure difference between the feed solution 14 and the permeate solution 16, as previously discussed. The entire multi-well plate may be placed on an oscillating table or other device for stirring or mixing the feed solution and the permeate solution. Alternatively, a stir bar or other device can be used to stir the feed solution and/or permeate solution, as previously discussed. Alternatively, the feed solution can be placed into the filter wells and the permeate solution can be placed into the acceptor wells. Thus, when the filter plate 106 is placed onto the acceptor plate 104, the feed solution is in fluid communication with the top side (that is, the feed side) of the microporous membrane 112, while the permeate solution (that is, the organic fluid) is in fluid communication with the bottom side (that is, the permeate side) of the microporous membrane 112.

The membrane-permeation test of the present invention is preferably performed under constant temperature conditions. This may be achieved by placing the device used to perform the test in a temperature-controlled chamber. Preferably, the test is performed at a physiologically relevant temperature, such as at about 37° C.

Method for Performing the Test

The method of the present invention comprises the following steps. A pharmaceutical composition is administered to an aqueous solution to form a feed solution. The pharmaceutical composition comprises a drug, as described below. By "administered" is meant that the pharmaceutical composition is placed in, dissolved in, suspended in, or otherwise delivered to the aqueous solution. The aqueous solution can be any physiologically relevant solution, such as phosphate buffered saline (PBS), simulated intestinal buffer without enzymes (SIN), a Model Fasted Duodenal (MFD) solution, or a solution to model the fed state. An appropriate PBS solution is an aqueous solution comprising 20 mM sodium phosphate ($Na_2HPO_4$), 47 mM potassium phosphate ($KH_2PO_4$), 87 mM NaCl, and 0.2 mM KCl, adjusted to pH 6.5 with NaOH. An appropriate SIN solution is 50 mM $KH_2PO_4$ adjusted to pH 7.4. An appropriate MFD solution is the same PBS solution wherein additionally is present 7.3 mM sodium taurocholic acid and 1.4 mM of 1-palmitoyl-2-oleyl-sn-glycero-3-phosphocholine. An appropriate solution to model the fed state is the same PBS solution wherein additionally is present 29.2 mM sodium taurocholic acid and 5.6 mM of 1-palmitoyl-2-oleyl-sn-glycero-3-phosphocholine. After forming the feed solution, the solution may be agitated to dissolve or disperse the pharmaceutical composition therein or may be added immediately to the feed solution reservoir. Alternatively, the feed solution may be prepared directly in the feed solution reservoir. Preferably, the solution is not filtered or centrifuged to remove undissolved species after administration of the pharmaceutical composition prior to performing the membrane-permeation test. In this way, all drug-containing species will be present in the feed. When the pharmaceutical composition is a dosage form, the dosage form is simply placed in the feed solution in the feed reservoir and stirred.

The feed solution is in contact with the feed side of a microporous membrane, described herein. As previously described, a portion of the walls of the pores proximate to the feed side of the membrane are hydrophilic. The portion of the pores of the membrane that are not hydrophilic are substantially filled with an organic fluid, and the permeate side of the membrane is in fluid communication with a permeate solution comprising the organic fluid. Both the feed solution and the organic fluid remain in contact with the microporous membrane for the duration of the test. The length of the test may range from several minutes to several hours or even days.

The rate of transport of drug from the feed solution to the permeate solution is determined by measuring the concentration of drug in the organic fluid in the permeate solution as a function of time or by measuring the concentration of drug in the feed solution as a function of time, or both. This can be accomplished by methods well known in the art, including by use of ultraviolet/visible (UV/Vis) spectroscopic analysis, high-performance liquid chromatography (HPLC), gas chromatography (GC), nuclear magnetic resonance (NMR), infra red (IR) spectroscopic analysis, polarized light, density, and refractive index. The concentration of drug in the organic fluid can be determined by sampling the organic fluid at discrete time points and analyzing for drug concentration or by continuously analyzing the concentration of drug in the organic fluid. For continuous analysis, UV/Vis probes may be used, as can flow-through cells. In all cases, the concentration of drug in the organic fluid is determined by comparing the results against a set of standards, as well known in the art. Measuring the concentration of drug in the feed solution as a function of time can be difficult for formulations that form a large amount of precipitate. One skilled in the art will realize that any analysis technique used to determine the concentration of drug in the feed should account for all species present in the feed, not just dissolved drug. Because of this, it is generally preferred to measure the concentration of drug in the organic fluid.

During the test, drug permeates across the membrane from the feed solution into the organic fluid. Without wishing to be bound by any particular theory or mechanism, it is believed that drug first diffuses across the unstirred water layer on the feed side of the membrane. Virtually any drug-containing species may contribute to transport across the unstirred water layer, including dissolved drug, drug in micelles, drug present in high-energy drug species, and small particles of drug or drug-containing solids, that is, precipitate. Any one or all of these species may contribute to the transport of drug across the unstirred water layer on the feed side of the membrane.

Once across the unstirred water layer, the drug partitions into the organic fluid that is present in the pores of the microporous membrane. Without wishing to be bound by any particular theory or mechanism, it is believed that the concentration of drug in the organic fluid at the organic fluid/feed solution interface is proportional to the dissolved drug concentration in the feed solution at the organic fluid/feed solution interface. In the case of ionizable drugs, it is believed that primarily the neutral form of the drug partitions into the organic fluid. Drug in other drug-containing species that cross the unstirred water layer will generally first convert to dissolved drug (in the aqueous feed solution) prior to drug partitioning into the organic fluid. Once partitioned into the organic fluid, the drug permeates through the microporous membrane, and ultimately into the organic fluid in the permeate solution.

For pharmaceutical compositions where the rate of dissolution of drug is relatively fast, the rate at which drug permeates the membrane (i.e., the rate at which drug is removed from the feed solution or appears in the permeate solution) is equal to an overall permeability coefficient ($P_{ov}$) (which is a function of the properties of the microporous membrane and the various species present in the feed) times a driving force related to the concentration of dissolved drug in the feed solution. Mathematically, this may be expressed by the following equation $$\dot{m} = V_p \frac{d[D]_p}{dt} = a_m P_{ov}\left([D_{dissolved}]_f - \frac{[D]_p}{k_{p,mem}}\right), \quad (1)$$

where $\dot{m}$ is the rate at which drug is transported across the membrane (g/sec), $V_p$ is the volume of the permeate solution (cm$^3$), $[D]_p$ is the concentration of drug in the permeate solution (g/cm$^3$), t is the time (sec), $a_m$ is the membrane area (cm$^2$), $P_{ov}$ is the overall permeability coefficient (cm/sec), $[D_{dissolved}]_f$ is the concentration of dissolved drug in the feed solution (g/cm$^3$), and $k_{p,mem}$ is the partition coefficient of drug between the organic fluid and water, which is defined as the ratio of (1) the concentration of drug in the organic fluid, and (2) the concentration of dissolved neutral drug in the aqueous feed solution when the two solutions are at equilibrium. The partition coefficient can be estimated from the ratio of (1) the solubility of drug in the organic fluid and (2) the solubility of the dissolved drug in the aqueous feed solution.

As previously indicated, the overall permeability coefficient, $P_{ov}$, is a function of the properties of the microporous membrane and the species present in the feed solution. For pharmaceutical compositions where the rate of dissolution of drug is relatively fast, the overall permeability coefficient can be expressed as follows:

$$\frac{1}{P_{ov}} = \frac{1}{P_m} + \frac{1}{P_{wl}},$$

where $P_m$ is the permeability coefficient for transport of drug through the membrane (cm/sec), which is a function of the thickness, porosity, pore size, and diffusivity of drug through the membrane; and $P_{wl}$ is the permeability coefficient for transport of drug through the unstirred water layer (cm/sec). The permeability coefficient for transport of drug through the unstirred water layer, $P_{wl}$, will be a function of the various species present in the feed solution. For example, for a feed solution containing dissolved drug and drug in bile salt micelles, the permeability coefficient for transport of drug through the unstirred water layer may be expressed as:

$$P_{wl} = P_{dissolved} + P_{micelles},$$

where $P_{dissolved}$ is the permeability coefficient for the transport of dissolved drug through the unstirred water layer (cm/sec), and $P_{micelles}$ is the permeability coefficient for the transport of drug present in bile-salt micelles through the unstirred water layer (cm/sec). Thus, for example, a pharmaceutical composition that results in a greater amount of drug in bile salt micelles will have a higher overall permeability coefficient than a composition that results in a lower amount drug in bile salt micelles, resulting in a higher rate of transport of drug across the membrane.

As discussed below, the organic fluid is selected to act as a sink for the drug, such that $k_{p,mem}$ is large, meaning that the last term in Equation 1 is small relative to the first term at short times, and can therefore usually be neglected when considering transport of the first 50 to 90% of the initial dose of drug. Thus, the rate at which drug permeates the membrane is approximately proportional to the dissolved drug concentration in the feed, as follows:

$$\dot{m} = V_p \frac{d[D]_p}{dt} \approx a_m P_{ov}[D_{dissolved}]_f. \quad (2)$$

One parameter obtained from the membrane-permeation test that is useful for characterizing the performance of a pharmaceutical composition is the maximum flux. The "maximum flux" is defined as follows:

$$\text{Maximum Flux} = \frac{\dot{m}_{max}}{a_m} \quad (3)$$
$$= \left[\frac{V_p}{a_m} \frac{d[D]_p}{dt}\right]_{max}$$
$$\approx P_{ov}[D_{dissolved}]_{f,max}.$$

In practical terms, the maximum flux is calculated by multiplying the maximum slope of the concentration of drug in the permeate solution versus time plot by the permeate volume and dividing by the membrane area. This maximum slope is typically determined during the first 10 to 240 minutes of the test, where the concentration of drug in the permeate solution often increases at a nearly constant rate following a time lag of a few minutes. In some cases the time lag can be as long as 90 minutes or more; in such cases, the maximum flux may be determined over an appropriate time interval. At longer times, as more of the drug is removed from the feed solution, the slope of the concentration versus time plot decreases, becoming non-linear. Often, this slope approaches zero as the driving force for transport of drug across the membrane approaches zero; that is, the drug in the two phases approaches equilibrium. The maximum flux is determined either from the linear portion of the concentration versus time plot, or is estimated from a tangent to the concentration versus time plot at the time where the slope is at its highest value if the curve is non-linear.

The maximum flux is useful for comparing pharmaceutical compositions containing the same drug. That is, by testing a series of compositions of a particular drug by dosing the compositions to feed solutions of the same components and utilizing the same type of membrane and permeate solution, the composition that provides the highest maximum flux can be identified. Without wishing to be bound by any particular theory or mechanism of action, it is believed that the higher the maximum flux provided by a composition, the higher the dissolved drug concentration generated in solution by that composition (that is, $[D_{dissolved}]_f$ is higher) or the faster drug is transported through the unstirred water layer (that is, $P_{ov}$ is higher), or both. In either case, the higher the maximum flux, the higher the expected rate of absorption in vivo. It is believed that a composition that provides a higher maximum flux for a given composition will provide a higher rate of absorption in vivo. A higher rate of absorption will, in turn, generally result in a higher bioavailability relative to a composition that provides a lower maximum flux for the same drug, as long as the compositions are dosed at a high enough level that absorption is incomplete and the high dissolved drug generated by the composition is sustained for a sufficiently long time.

Another useful method for evaluating pharmaceutical compositions is to compare the fraction or percentage of drug removed from the feed after a given time period. For many pharmaceutical compositions, the concentration of drug decreases over time. Such compositions may provide a high maximum flux of drug in the membrane permeation test due to the higher enhancement of the dissolved drug concentration. However, because the dissolved-drug enhancement is only temporary, the rate at which drug permeates the membrane decreases as the dissolved drug concentration decreases. Therefore, a comparison of the fraction of drug removed from the feed solution after a given period of time may provide a more accurate indication of the performance of various compositions in vivo compared to using the maximum flux as an indicator. Without wishing to be bound by any particular theory or mechanism of action, it is believed that a pharmaceutical composition that results in a higher fraction of drug removed from the feed in the membrane-permeation test over a biologically relevant time, such as 2 to 10 hours, generally will provide a higher bioavailability than a composition that results in a lower fraction of drug removed from the feed over the same time period. The time period for comparison of the compositions may be any time that is practical for comparison of the compositions, such as 1 hour, 2 hours, 4 hours, etc. Preferably, the compositions are compared after a period of time that is representative of the GI transmit time, such as 2 hours to 10 hours, and preferably 3 to 8 hours.

The Membrane

The membrane-permeation test utilizes a microporous membrane. By "microporous" is meant that the membrane contains a plurality of small pores. Preferably, the nominal pore size ranges from about 0.01 µm to about 10 µm, more preferably, from about 0.01 to about 1 µm, even more preferably from about 0.02 to about 0.5 µm, even more preferably from about 0.05 to about 0.45 µm, and most preferably from about 0.1 to about 0.2 µm. Most manufacturers provide information on the nominal pore sizes of membranes, and procedures for determining the pore size of a microporous membrane are well known in the art (see, for example, Membrane Handbook, Ho and Sirkar, editors, 1992). Microporous membranes suitable for use in the test are available from several manufacturers, including the ACCUREL® membranes from Membrana GmbH (Wuppertal, Germany), the DURAPORE®, FLUOROPORE™, and MITEX™ membranes from Millipore Corporation (Billerica, Mass.), the CELGARD® membranes from Celgard, Inc. (Charlotte, N.C.), the EMFLON®, METRICEL®, ZEFLUOR™, and TF (PTFE) membranes from Pall Corporation (Ann Arbor, Mich.); and the PTFE membranes from Sartorius AG (Germany).

The microporous membrane is preferably made from a hydrophobic material. By "hydrophobic" is meant that the contact angle of a drop of water placed on the membrane is greater than about 90°, preferably greater than about 100°. Procedures for measurement of contact angles on the surface of a membrane are well known in the art. Examples of suitable materials for the hydrophobic microporous membrane include polypropylene, polyethylene, polytetrafluoroethylene (Teflon® or PTFE), polyvinylidine difluoride (PVDF), and polysulfone.

The microporous membrane preferably has a high "porosity," meaning that the number or frequency of pores on the membrane surface is large. Preferably, the porosity of the membrane is at least about 20%, more preferably at least about 30%, and most preferably at least about 40%. Standard techniques in the art, such as the use of scanning electron microscopy, can be used to determine the porosity of a microporous membrane, and manufacturers routinely report membrane porosity. See Ho and Sirkar, *Membrane Handbook,* 1992.

The microporous membrane may be symmetric or asymmetric, isotropic or anisotropic. When the membrane is asymmetric, it is preferred that the surface with the small pores be the feed side of the membrane and the surface with the larger pores be the permeate side of the membrane.

The microporous membrane may be in the form of a flat sheet or disc, or in the form of a hollow-fiber or tube. When in the form of a hollow-fiber or tube, the feed side of the membrane may be on the outside of the fiber or tube, or the inside of the fiber or tube.

In a preferred embodiment, the membrane is a flat sheet Accurel® PP 1E microporous polypropylene membrane, available from Membrana GmbH, Wuppertal, Germany, having a nominal pore size of 0.1 µm.

Hydrophilic Surface

Although the microporous membrane is preferably made from a hydrophobic material, the feed side of the membrane is hydrophilic. By "hydrophilic" is meant that the contact angle of a drop of water placed on the feed side of the membrane is less than about 70°, preferably less than about 60°, and most preferably less than about 50°.

The feed side of the membrane may be rendered hydrophilic by any method that results in a contact angle of a drop of water placed on the feed side of the membrane meeting the above criteria. The feed side of the membrane may be rendered hydrophilic by a process that results in the pores on the feed side of the membrane being occluded, or not occluded. In one method, a portion of the walls of the microporous membrane proximate to the feed side that define the pores of the membrane are hydrophilic. In another method, a hydrophilic coating may be applied to the feed side of the hydrophobic, microporous membrane. By "a portion" is meant that the wall that defines the pore is not hydrophilic throughout the entire depth of the pore. In other words, the walls of the pore are not hydrophilic across the entire thickness of the membrane. Rather, the walls of the pore are hydrophilic near the feed-side surface of the membrane. Preferably, the depth of the walls of the pore that is hydrophilic is no more than about half the thickness of the membrane. More preferably, the depth of the walls of the pore that is hydrophilic is no more than about a quarter the thickness of the membrane. In a preferred embodiment, the depth of the walls of the pore that is hydrophilic is no more than about 10 µm, more preferably no more than about 5 µm, and even more preferably no more than about 2 µm.

In one embodiment, the membrane is treated to render the feed side of the membrane hydrophilic. By "treated" is meant that the feed side of the membrane is modified to render the surface of the membrane and a portion of the walls of the pores near the surface hydrophilic, such as by application of a coating, absorption or adsorption of a hydrophilic material to the surface of the membrane and walls of the pores, or attachment of hydrophilic groups or substituents to the surface of the membrane and a portion of the walls of the pores. It is to be understood by those skilled in the art that such treatment does not occlude the pores on the surface of the membrane or result in the formation of a non-porous layer or surface on the feed side of the membrane, but rather, the feed side of the membrane retains a microporous structure.

In one embodiment, the feed side of the membrane is treated using a cold plasma. In this process, the membrane is first thoroughly cleaned and then dried. The membrane is then placed into a plasma chamber such that the feed side of the membrane is exposed to the plasma while the permeate side of the membrane is placed against a surface or otherwise masked to prevent exposure to the plasma. The plasma chamber is held at low pressure, typically less than about 800 mtorr. A radio frequency (RF) generator or other means is then used to form the plasma. The membrane is exposed to the plasma for a sufficiently long time to render the feed side of the membrane hydrophilic. The plasma chamber, under low pressure, preferably contains components that will result in hydrophilic species being attached to the membrane. Examples of such components include water, oxygen, ammonia, methanol, and ethanol. Preferably, the plasma chamber contains water vapor.

For example, a 0.1-µm Accurel® PP 1E membrane may be treated using the following procedure. First, the membrane is washed in isopropyl alcohol and in methanol and then dried. The membrane is then placed into a glass-walled plasma chamber with the permeate side of the membrane against the glass wall. The plasma chamber is saturated with water vapor held at a pressure of 550 mtorr. An RF generator is used to form the plasma at an energy input of 50 watts. The membrane is positioned such that only the feed side of the membrane is exposed to the plasma. The membrane is treated for 45 seconds, after which it is removed from the plasma chamber. The contact angle of a drop of water placed on the treated surface of the membrane is then determined to be less than about 70°.

In another embodiment, the feed side of the membrane is treated with a solution that attaches hydrophilic groups to the surface of the membrane. For example, U.S. Pat. No. 5,476,590, incorporated herein by reference, discloses that PVDF membranes can be made hydrophilic by treating the same with a caustic solution, followed by treating it with a second solution to attach hydrophilic groups to the membrane surface. Such processes can be used to treat the surface of the membrane by first filling the pores of the membrane with a material that will retard penetration of the treatment solution deep into the pores of the membrane. This material can be removed in a subsequent step once the surface has been rendered hydrophilic.

In yet another embodiment, a material may be absorbed or adsorbed to the surface of the membrane to render it hydrophilic. Preferably, the material absorbed or adsorbed to the surface has a low solubility in the feed solution. Low solubility is preferred to provide stability of the hydrophilic surface, and to ensure the absorbed material does not leach into the feed solution, thus affecting the results of the test.

In yet another embodiment, a coating is applied to the surface of the microporous membrane. Preferably the coating does not occlude, cover, or block the pores of the microporous membrane. Rather, the coating results in a thin coating layer on the surface of the membrane and on the inside walls of the pores of the membrane near the feed side of the membrane. The coating material preferably has a low solubility in the feed solution and in the organic fluid. Most preferred are crosslinked materials that are essentially insoluble in aqueous and organic solutions. Examples of materials suitable for use as the coating include crosslinked hydrogel-forming materials, such as crosslinked polyvinylpyrrolidone (also known as crospovidone); crosslinked polyvinylalcohol, water-insoluble cellulosic materials, such as ethylcellulose; water-insoluble acrylate, methacrylate, and methylmethacrylate copolymers; siloxanes and silanes; and crosslinked polyamides, polyureas, polyurethanes, polyimides, polyesters, and polyethers. The coating may also contain additives to render the material more hydrophilic or to adhere the coating to the microporous membrane material. Such additives may be removed from the coating after formation, or may be an integral part of the coating.

In still another embodiment, the membrane comprises two separate and distinct layers: (a) a hydrophilic microporous layer that acts as the feed side of the membrane; and (b) a hydrophobic microporous layer that acts as the permeate side of the membrane. Such "composite" membranes are well known in the art and can be made by a variety of techniques, also well known in the art. In one embodiment, the composite membrane comprises a hydrophilic membrane and a hydrophobic membrane sandwiched together. In another embodiment, a hydrophilic microporous membrane is formed in situ on a hydrophobic microporous membrane.

According to the second approach for rendering the feed side of the membrane hydrophilic, a hydrophilic coating is applied to the feed side of the hydrophobic membrane such that the at least a portion of the pores of the membrane are covered, blocked or occluded. However, it is critical that the coating be sufficiently swollen by the aqueous feed solution that the coating is highly permeable to the species that have molecular weights up to about 1000 daltons, such as the dissolved drug. Preferably, the coating will be sufficiently swollen with the aqueous feed solution that it is highly permeable to species up to about 10 to 20 nm in size. Thus, it is preferred that the coating be permeable to drug-containing micelles such as those present in MFD solution or a solution to model the fed state, as previously described. Thus, the preferred coatings may be comprised of "hydrogel" materials. By "hydrogel" is meant any polymer that in contact with the aqueous feed solution is comprised of greater than about 50 wt % water, preferably greater than about 65 wt % water. Exemplary water-swollen polymers include crosslinked or non-crosslinked forms of proteins, polypeptides, and polysaccharides.

Without wishing to be bound by any particular theory or mechanism of action, it is believe that utilizing a membrane wherein the feed side of the membrane is hydrophilic provides several advantages to the inventive membrane-permeation test over the prior art. First, the hydrophilic surface on the feed side of the membrane results in a very thin layer of material that is wetted by the feed solution. This provides a uniform-thickness unstirred water layer on the feed side of the membrane. This will minimize the effects any variations in stirring of the feed solution will have on the thickness of the unstirred water layer.

Second, the hydrophilic surface results in the interface between the feed solution and the organic fluid being located within the thickness of the membrane, rather than on the surface of the membrane. This has the advantage of preventing species in the feed solution (such as small drug-containing particles) coming into direct contact with the organic fluid, resulting in permeation rates that are not representative of what occurs in vivo.

The inventors recognized the problem that when the membrane does not have a hydrophilic surface, the organic fluid may be present on the surface of the membrane. During tests with such membranes, large (greater than about 1 μm in diameter) drug-containing particles can impinge on the organic fluid on the membrane surface. As a result, the drug in the particle can dissolve directly into the organic fluid, rather than first converting to dissolved drug and then being absorbed into the organic fluid. The inventors solved this problem by utilizing a membrane with a hydrophilic surface that prevents direct contact of large drug-containing particles with the organic fluid.

The Organic Fluid

The portions of the pores of the microporous membrane that are not hydrophilic contain an organic fluid. The permeate reservoir also contains the organic fluid. The organic fluid is substantially immiscible with water and acts as a sink for the drug. By "substantially immiscible" means that the organic fluid forms two phases when mixed with an aqueous solution. By "acts as a sink for the drug" is meant that the solubility of drug in the organic fluid is high relative to the solubility of drug in water. Preferably, the partition coefficient of drug between the organic fluid and water, $k_{p,mem}$, which is defined as the ratio of (1) the concentration of drug in the organic fluid, and (2) the concentration of dissolved neutral drug in the aqueous feed solution when the two solutions are at equilibrium, is at least 5, more preferably at least about 10, and even more preferably at least about 20. For some hydrophobic drugs, such as those with Log P values of about 3 or greater, the partition coefficient can be even higher, such as 100, 1,000, 10,000, 100,000, 500,000, up to 1,000,000, or more.

The organic fluid is preferably a liquid at 37° C. and preferably has a low volatility to reduce evaporative losses of the fluid during the test. Virtually any compound or mixture of compounds can be used as the organic fluid, provided it is water immiscible and has a high $k_{p,mem}$. Compounds that can be used as the organic fluid include alkanes, alkenes, alcohols, ethers, ketones, aromatics, alkyl halides, and mixtures thereof. By "alkanes" is meant straight chain, branched, or cyclic saturated hydrocarbons. Exemplary alkanes include hexane, heptane, octane, decane, dodecane, hexadecane, cyclopentane, cyclohexane, and mixtures thereof. By "alkenes" is meant straight chain, branched, and cyclic unsaturated hydrocarbons. Exemplary alkenes include 1,6-heptadiene, 1,7-octadiene, 1,8-nonadiene, 1-9-decadiene, and mixtures thereof. By "alcohols" is meant straight chain, branched, or cyclic hydrocarbons having at least one alcohol substituent. Exemplary alcohols include octanol, decanol, dodecanol, isoamyl alcohol, cyclohexanol, 2-ethylhexanol, 2,6-dimethyl-4-heptanol, and mixtures thereof. By "ethers" is meant straight chain, branched, or cyclic hydrocarbons having at least one ether substituent. Examples of ethers include isopropyl ether, n-butyl ether, methyl-isobutyl ether, di-isopropyl ether, methyl-tert-butyl ether, ethyl-tert-butyl ether, di-tert-butyl ether, dibutyl ethylene glycol, and mixtures thereof. By "ketones" is meant straight chain, branched, or cyclic hydrocarbons having at least one ketone group. Examples of ketones include methyl n-butyl ketone, methyl isobutyl ketone, methyl amyl ketone, methyl isoamyl ketone, diisobutyl ketone, ethyl isobutyl ketone, pentanone, hexanone, octanone, cyclohexanone, isophorone, and mixtures thereof. By "aromatics" is meant a hydrocarbon having at least one aromatic ring. Examples of aromatics include benzene, toluene, the various isomers of xylene, ethyl benzene, nitrobenzene, nitrotoluene, cresol, and mixtures thereof. By "alkyl halides" is meant a hydrocarbon having at least one halide substituent. Examples of alkyl halides include methylene chloride, chloroform, carbon tetrachloride, perchloroethylene, trichloroethylene, trichloro-trifluoroethylene, tetrachloroethane, trichloroethane, dichloroethane, dibromoethane, propylene dichloride, chlorobenzene, dichlorobenzene, chlorotoluene, and mixtures thereof.

In one embodiment, the organic fluid is an alkane having at least 6, preferably at least 7, more preferably at least 8 carbon atoms. In another embodiment, the organic fluid is an alcohol having at least 6, preferably at least 7, more preferably at least 8 carbon atoms. In yet another embodiment, the organic fluid is selected from the group consisting of alkenes having at least 6, preferably at least 7, more preferably at least 8 carbon atoms. In yet another embodiment, the organic fluid is selected from the group consisting of alkanes having at least 6, preferably at least 7, more preferably at least 8 carbon atoms, alcohols having at least 6, preferably at least 7, more preferably at least 8 carbon atoms, alkenes having at least 6, preferably at least 7, more preferably at least 8 carbon atoms, and mixtures thereof. In yet another embodiment, the organic fluid is selected from the group consisting of alkanes having at least 8 but no more than 20 carbon atoms, alcohols having at least 8 but no more than 20 carbon atoms, alkenes having at least 8 but no more than 20 carbon atoms, and mixtures thereof. In still another embodiment, the organic fluid is a mixture of at least one alkane having from 8 to 12 carbon atoms and at least one alcohol having from 8 to 12 carbon atoms. One preferred organic fluid is a mixture of decanol and decane.

The organic fluid may also contain additives to adjust the solubility and permeability of the drug and the properties of the organic fluid. Examples include phospholipids, such as egg lecithin, soy lecithin, phosphatidylcholine, dioleoylphosphatidylcholine, phosphatidylserine, phosphatidylinositol, phosphatidylethanolamine; cholesterol; triglycerides; organic acids, such as stearic acid; and mixtures thereof.

Pharmaceutical Compositions

The pharmaceutical composition evaluated in the membrane-permeation test of the present invention comprises a drug. The pharmaceutical composition can consist of drug alone, or it can comprise a drug and at least one excipient. The pharmaceutical composition can be in the form of a solid, including powders, granules, particles, pastes, tablets, capsules, or other solid forms known in the art, or in the form of a liquid, including drug dissolved or suspended in a solvent or liquid, as known in the art. The term "drug" is conventional, denoting a compound having beneficial prophylacetic and/or therapeutic properties when administered to an animal, especially humans. This includes, without limitation, inorganic and organic compounds that act on the peripheral nerves, adrenergic receptors, cholinergic receptors, nervous system, skeletal muscles, cardiovascular smooth muscles, blood circulatory system, synaptic sites, neuroeffector junctional sites, endocrine and hormone systems, immunological system, reproductive system, autocoid systems, alimentary and excretory systems, inhibitors of autocoids and histamine systems. Preferred classes of drugs include, but are not limited to, antihypertensives, antianxiety agents, anticlotting agents, anticonvulsants, blood glucose-lowering agents, deconges- tants, antihistamines, antitussives, antineoplastics, beta blockers, anti-inflammatories, antipsychotic agents, cognitive enhancers, cholesterol-reducing agents, anti-atherosclerotic agents, antiobesity agents, autoimmune disorder agents, anti-impotence agents, antibacterial and antifungal agents, hypnotic agents, anti-Parkinsonism agents, anti-Alzheimer's disease agents, antibiotics, anti-depressants, antiviral agents, glycogen phosphorylase inhibitors, cholesteryl ester transfer protein inhibitors, vitamins, and minerals. Veterinary drugs may also be suitable for use with the present invention.

The membrane-permeation test of the present invention is particularly well suited for evaluation of low-solubility drugs and compositions that improve or enhance, at least temporarily, the aqueous concentration or solubility of such drugs. By "low-solubility" is meant that the drug has a minimum aqueous solubility at physiologically relevant pH (e.g., pH 1-8) of about 1 mg/mL or less. The invention finds greater utility as the aqueous solubility of the drug decreases. Thus, drug may have an aqueous solubility of less than about 0.5 mg/mL, less than about 0.1 mg/mL, less than about 0.05 mg/mL, and even less than about 0.01 mg/mL. In general, it may be said that the drug has a dose-to-aqueous solubility ratio greater than about 10 mL, and more typically greater than about 100 mL, where the aqueous solubility (mg/mL) is the minimum value observed in any physiologically relevant aqueous solution (e.g., those with pH values between 1 and 8) including USP simulated gastric and intestinal buffers, and dose is in mg. Thus, a dose-to-aqueous solubility ratio may be calculated by dividing the dose (in mg) by the aqueous solubility (in mg/mL).

The membrane-permeation test of the present invention is also particularly well suited for evaluation of hydrophobic drugs. By "hydrophobic drugs" is meant drugs that have a Log P value of at least 2.0. Log P, defined as the base 10 logarithm of the ratio of (1) the drug concentration in an octanol phase to (2) the drug concentration in a water phase when the two phases are in equilibrium with each other, is a widely accepted measure of hydrophobicity. Log P may be measured experimentally or calculated using methods known in the art. The Log P may be estimated experimentally by determining the ratio of the drug solubility in octanol to the drug solubility in water. When using a calculated value for Log P, the highest value calculated using any generally accepted method for calculating Log P is used. Calculated Log P values are often referred to by the calculation method, such as Clog P, Alog P, and Mlog P. The Log P may also be estimated using fragmentation methods, such as Crippen's fragmentation method (*J. Chem. Inf. Comput. Sci.,* 27, 21 (1987)); Viswanadhan's fragmentation method (*J. Chem. Inf. Comput. Sci.,* 29, 163 (1989)); or Broto's fragmentation method (*Eur. J. Med. Chem.-Chim. Theor.,* 19, 71 (1984). Preferably the Log P value is calculated by using the average value estimated using Crippen's, Viswanadhan's, and Broto's fragmentation methods. The membrane-permeation test generally finds greater utility as the Log P value of the drug increases.

The membrane-permeation test of the present invention is particularly well suited for evaluating pharmaceutical compositions that, at least temporarily, enhance, increase, or otherwise improve the dissolution rate or aqueous concentration of low-solubility drugs.

The drug in the pharmaceutical composition can be in any pharmaceutically acceptable form. By "pharmaceutically acceptable form" is meant any pharmaceutically acceptable derivative or variation, including stereoisomers, stereoisomer mixtures, enantiomers, solvates, hydrates, isomorphs, polymorphs, pseudomorphs, neutral forms, salt forms and prodrugs. The drug may be in any physical state, including crystalline, semi-ordered, liquid crystalline, amorphous, other non-crystalline forms, or a mixture of any or all of these states. The drug in the composition can be in any physical form, including particles, granules, microparticles, nanoparticles, micronized drug (crystalline or non-crystalline), flakes, needles, pellets, and powders. The drug may even be dissolved in a liquid or semi-solid vehicle; the resulting composition may then dissolve, disperse, or be emulsified upon addition to the feed solution, so long as any excipients present in the composition, such as surfactants, do not affect the membrane.

The pharmaceutical composition may optionally include one or more excipients. Examples of excipients, well known in the art, include matrix materials, complexing agents, fillers, disintegrating agents (disintegrants), and binders. Examples of matrix materials, fillers, or diluents include lactose, mannitol, xylitol, microcrystalline cellulose, dibasic calcium phosphate (dihydrate and anhydrous), and starch. Examples of disintegrants include sodium starch glycolate, sodium alginate, carboxy methyl cellulose sodium, methyl cellulose, and croscarmellose sodium, and crosslinked forms of polyvinyl pyrrolidone such as those sold under the trade name CROSPOVIDONE (available from BASF Corporation). Examples of binders include methyl cellulose, microcrystalline cellulose, starch, and gums such as guar gum, and tragacanth. Examples of lubricants include magnesium stearate, calcium stearate, and stearic acid. Examples of preservatives include sulfites (an antioxidant), benzalkonium chloride, methyl paraben, propyl paraben, benzyl alcohol and sodium benzoate. Examples of suspending agents or thickeners include xanthan gum, starch, guar gum, sodium alginate, carboxymethyl cellulose, sodium carboxymethyl cellulose, methyl cellulose, hydroxypropyl methyl cellulose, polyacrylic acid, silica gel, aluminum silicate, magnesium silicate, and titanium dioxide. Examples of anticaking agents or fillers include silicon oxide and lactose. Other conventional excipients may be employed in the compositions of this invention, including those excipients well-known in the art. Generally, excipients such as pigments, lubricants, flavorants, and so forth may be used for customary purposes and in typical amounts. See *Remington: The Science and Practice of Pharmacy*, 20$^{th}$ Edition, (2000).

In one embodiment, the pharmaceutical composition is in the form of a solid amorphous dispersion of a drug in a concentration-enhancing polymer. Such dispersions are disclosed in commonly owned, co-pending U.S. patent application Ser. No. 09/131,019, which published as U.S. Patent Application Publication No. 20020009494, U.S. patent application Ser. No. 09/495,049, U.S. patent application Ser. No. 10/175,132, which published as U.S. Patent Application Publication No. 20030091643, U.S. patent application Ser. No. 10/175,566, which published as U.S. Patent Application Publication No. 20020054038, U.S. patent application Ser. No. 10/175,945, which published as U.S. Patent Application Publication No. 20030170309, all of which are incorporated herein by reference.

In another embodiment, the pharmaceutical composition comprises an adsorbate of a drug and a solid substrate. Such compositions are disclosed in commonly owned, co-pending U.S. patent application Ser. No. 10/173,987, which published as U.S. Patent Application Publication No. 20030054037, the disclosure of which is incorporated herein by reference.

In another embodiment, the pharmaceutical composition comprises a mixture of a drug and a concentration-enhancing polymer. Such compositions are disclosed U.S. Pat. No. 6,548,555, and in commonly owned, co-pending U.S. patent application Ser. No. 09/742,785, which published as U.S. Patent Application Publication No. 20020006443, U.S. patent application Ser. No. 10/175,640, which published as U.S. Patent Application Publication No. 20030104063, and U.S. patent application Ser. No. 10/176,462, which published as U.S. Patent Application Publication No. 20030072801, the disclosures of which are incorporated herein by reference.

The pharmaceutical composition may also be in the form of a dosage form. Examples of dosage forms include tablets, capsules, pills, caplets, suppositories, suspensions, powders for suspension, sachets, creams, transdermal patches, depots, and the like, all well-known in the art. See *Remington: The Science and Practice of Pharmacy*, 20$^{th}$ Edition, (2000).

As previously described, the pharmaceutical composition is administered to an aqueous solution to form a feed solution. The aqueous solution can be any physiologically relevant solution, such as phosphate buffered saline (PBS), simulated intestinal buffer without enzymes (SIN), a Model Fasted Duodenal (MFD) solution, or a solution to model the fed state. An appropriate PBS solution is an aqueous solution comprising 20 mM sodium phosphate ($Na_2HPO_4$), 47 mM potassium phosphate ($KH_2PO_4$), 87 mM NaCl, and 0.2 mM KCl, adjusted to pH 6.5 with NaOH. An appropriate SIN solution is 50 mM $KH_2PO_4$ adjusted to pH 7.4. An appropriate MFD solution is the same PBS solution wherein additionally is present 7.3 mM sodium taurocholic acid and 1.4 mM of 1-palmitoyl-2-oleyl-sn-glycero-3-phosphocholine. An appropriate solution to model the fed state is the same PBS solution wherein additionally is present 29.2 mM sodium taurocholic acid and 5.6 mM of 1-palmitoyl-2-oleyl-sn-glycero-3-phosphocholine.

The pharmaceutical composition may be administered into the feed solution at any suitable concentration. The concentration may range from about 0.1 μg/mL or lower up to about 10,000 μg/mL or more. Typically, the concentration may range from about 1 μg/mL up to about 5,000 μg/mL. When the test is being performed to identify a composition that provides enhanced concentration and/or dissolution rate of a drug, the concentration should be sufficiently high that the anticipated enhancement can be observed. For example, if the composition is anticipated to enhance the dissolved drug concentration about 2-fold relative to crystalline drug, the feed concentration should be about 2-fold to 10-fold or more the equilibrium aqueous solubility of the crystalline drug.

In one embodiment, the membrane-permeation test of the present invention can be used to estimate the fed/fasted ratio obtained when a pharmaceutical composition is administered in vivo. In this embodiment, the pharmaceutical composition is tested in the membrane-permeation test using a feed solution modeling the fasted state, such as the MFD solution described above. The pharmaceutical composition is also tested in the membrane-permeation test using a feed solution modeling the fed state, such as the solution described above. A comparison of the maximum flux or the fraction or percentage of drug removed from the feed after a given time period or both provides an indication of the in vivo performance of the composition under fasted and fed conditions.

Without further elaboration, it is believed that one of ordinary skill in the art can, using the foregoing description, utilize the present invention to its fullest extent. Therefore, the following specific embodiments are to be construed as merely illustrative and not restrictive of the scope of the invention.

Those of ordinary skill in the art will understand that variations of the conditions and processes of the following examples can be used.

EXAMPLES

Preparation of a Microporous Membrane with a Hydrophilic Surface

A cold plasma was used to treat the feed side of a microporous membrane as follows. An Accurel® PP 1E microporous polypropylene membrane was obtained from Membrana GmbH (Wuppertal, Germany). This membrane has a nominal pore size of 0.1 µm, a thickness of about 92 µm, and a porosity of about 70%. The contact angle of a drop of water placed on the untreated membrane is greater than about 110°.

The membrane was rinsed five times in fresh isopropyl alcohol at room temperature for about 24 hours, for a total rinsing time of about 120 hours, and then allowed to air dry. Prior to treatment, the membrane was rinsed in methanol in a sonicating bath for 1 minute at ambient temperature, and then allowed to air dry at ambient temperature.

A sample of the membrane measuring about 10 cm by about 23 cm was placed into a glass-walled plasma chamber having an inside diameter of about 3 inches (7.5 cm). The membrane was positioned such that the permeate side of the membrane was against the glass wall of the plasma chamber. The atmosphere of the plasma chamber was saturated with water vapor at a pressure of 550 mtorr by placing a shallow tray of water into the chamber prior to reducing the pressure using a vacuum pump.

After achieving a constant pressure in the plasma chamber (about 3 to 5 minutes), the plasma was generated using radio frequency (RF) power inductively coupled into the chamber via annular electrodes. The power on the RF generator was set at 50 watts. The membrane was exposed to the plasma for 45 seconds, after which the power was turned off and the pressure in the chamber increased to ambient using air. The contact angle of a drop of water placed on the surface of the plasma-treated membrane was about 40°. The contact angle of a drop of water placed on the permeate side of the same membrane was greater than about 110°.

Example 1

The crystalline form of the cholesteryl ester transfer protein (CETP) inhibitor [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester, also known as torcetrapib ("Drug 1") was evaluated in a membrane-permeation test. An apparatus similar to the one shown schematically in FIG. 3 was assembled as follows. A permeate reservoir was formed by gluing a sample of the plasma-treated membrane described above to a glass tube having an inside diameter of about 1 inch (2.54 cm) using an epoxy-based glue (LOCTITE® E-30CL HYSOL® from Henkel Loctite Corp, Rocky Hill, Conn.). The feed-side of the membrane was oriented so that it was on the outside of the permeate reservoir, while the permeate-side of the membrane was oriented so that it was on the inside of the reservoir. The glue was allowed to set by placing the permeate reservoir in an oven at 50° C. and 25% relative humidity (RH) overnight. The contact angle of a drop of water on the feed side of the membrane after assembling the permeate reservoir was about 50°. The effective membrane area of the permeate reservoir was about 4.9 cm².

The pharmaceutical composition comprised 30 mg of crystalline Drug 1. The drug was added to 30 mL of PBS to form the feed solution. Thus, the concentration of drug in the feed solution would have been 1 mg/mL (1000 µg/mL) if all of the drug had dissolved. This is well in excess of the solubility of Drug 1 in water, estimated to be less than about 0.04 µg/mL. The feed solution was mixed on a vortex mixer for about 1 minute.

The organic fluid consisted of 4 mL of decanol, which was added to the permeate reservoir. The solubility of Drug 1 in decanol was measured to be in excess of 25 mg/mL. Thus, the partition coefficient of the drug between the organic fluid and PBS was greater than about 650,000. An overhead stirrer was used to stir the decanol permeate solution at 100 rpm.

The apparatus was assembled by first filling the permeate reservoir with the permeate solution. The permeate reservoir, with attached membrane, was placed within a glass feed reservoir about 3.3 cm in diameter such that the membrane was held about 1 cm above the bottom of the feed reservoir, and the membrane was wetted by the permeate solution. The feed reservoir was equipped with a magnetic stir bar and the reservoir was placed on a stir plate and adjusted to a stir rate of 600 rpm. Care was taken to ensure no air bubbles were trapped beneath the feed side of the membrane. Time 0 was taken as the time the permeate reservoir was placed within the feed solution reservoir such that the feed solution contacted the membrane surface. The membrane-permeation apparatus was placed into a 37° C. controlled-temperature chamber to maintain constant temperature.

A 100-µL sample of the decanol solution was removed from the permeate reservoir at 30 minutes following contact of the membrane with the feed solution and at the following time points: 60, 90, 120, 150, 210, 240, 270, 300, 330, 360, 390, 420, and 450 minutes following the start of the test. The samples were diluted 1:3.5 with methanol and analyzed via high-performance liquid chromatography (HPLC) at a UV absorbance of 256 nm using a Waters Symmetry C8 column and a mobile phase consisting of 15% (0.2% $H_3PO_4$)/85% methanol. Drug concentration was calculated by comparing UV absorbance of samples to the absorbance of drug standards. The concentration of Drug 1 obtained from these samples is shown in Table 1, which represents the average of duplicate tests.

TABLE 1

| Example | Time (min) | Drug 1 Concentration in Permeate (µg/mL) |
|---|---|---|
| 1 | 0 | 0.0 |
|   | 30 | 0.0 |
|   | 60 | 0.0 |
|   | 90 | 3.3 |
|   | 120 | 4.5 |
|   | 150 | 6.9 |
|   | 210 | 7.4 |
|   | 240 | 9.2 |
|   | 270 | 11.8 |
|   | 300 | 12.2 |
|   | 330 | 14.9 |
|   | 360 | 13.9 |
|   | 390 | 16.9 |
|   | 420 | 21.4 |
|   | 450 | 21.5 |

These results show that the concentration of Drug 1 in the permeate solution increased approximately linearly with time between 90 minutes and 210 minutes. The maximum flux of drug across the membrane (in units of µg/cm²-min) was determined by performing a least-squares fit to the data in Table 1 from 90 minutes to 210 minutes to obtain the slope (0.035 µg/mL-min), multiplying the slope by the permeate volume (4 mL) and dividing by the membrane area (4.9 cm²). The results of this analysis indicated that the "maximum flux" of Drug 1 through the membrane was 0.028 µg/cm²-min.

Example 2

A test was performed to demonstrate that the maximum flux of Drug 1 across the membrane does not change when the amount of drug added to the feed solution is changed. Example 2 was performed following the procedures outlined in Example 1 with the following exceptions. The feed solution consisted of 2.67 mg of crystalline Drug 1 in 30 mL PBS. Thus, the concentration of drug in the feed solution would have been 89 µg/mL if all of the drug had dissolved—still in excess of the aqueous solubility of Drug 1 in PBS (less than 0.04 µg/mL). A 4-mL sample of decanol was used as the organic fluid. Sample points were collected at the times given in Table 2. The maximum flux of drug was determined over the time interval from 80 to 160 minutes using the procedures outlined in Example 1 and the results are reported in Table 3, along with the results for Example 1 for comparison. These data demonstrate that the flux of drug is independent of the amount of drug added to the feed solution.

TABLE 2

| Example | Time (min) | Drug 1 Concentration in Permeate (µg/mL) |
|---|---|---|
| Example 2 | 0 | 0.0 |
|  | 20 | 0.0 |
|  | 40 | 0.0 |
|  | 60 | 0.0 |
|  | 80 | 1.7 |
|  | 100 | 2.2 |
|  | 120 | 3.0 |
|  | 140 | 3.7 |
|  | 160 | 4.0 |

TABLE 3

| Example | Composition | Amount of Drug 1 Added to the Feed (µg/mL) | Maximum Flux of Drug 1 (µg/cm²-min) |
|---|---|---|---|
| 1 | Crystalline Drug 1 | 1000 | 0.028 |
| 2 | Crystalline Drug 1 | 89 | 0.025 |

Comparative Example C1

This example demonstrates that performing the membrane-permeation test using a membrane that does not have a hydrophilic feed side results in high fluxes of a low-solubility drug across the membrane that are not indicative of in vivo performance.

A series of tests were performed using the procedure outlined in Example 1 except that an un-treated ACCUREL® PP 1E microporous polypropylene membrane was utilized in the test apparatus. The contact angle of a drop of water on the feed side of the membrane was greater than about 100°, and thus was hydrophobic. The flux of Drug 1 across the membrane was determined using the procedures outlined in Example 1 as a function of the amount of Drug 1 added to the feed solution. The results of these tests are summarized in Table 4 and show that the maximum flux of Drug 1 across the membrane was approximately proportional to the amount of Drug 1 added to the feed. Without wishing to be bound by any particular theory or mechanism of action, it is believed that without the hydrophilic surface, particles of crystalline drug contacted the permeate solution (decanol) directly and dissolved into the decanol permeate solution, resulting in high maximum fluxes of Drug 1 across the membrane. Thus, using a membrane that does not have a hydrophilic surface on the feed side does not yield a maximum flux that is proportional to the dissolved drug concentration and therefore is not expected to be predictive of in vivo performance for a hydrophobic drug.

TABLE 4

| Example | Conditions | Amount of Drug 1 Added to the Feed (µg/mL) | Maximum Flux of Drug (µg/cm²-min) |
|---|---|---|---|
| Comparative Example 1 | Un-treated Microporous Membrane | 25 | 0.75 |
|  |  | 50 | 1.5 |
|  |  | 80 | 4.0 |
|  |  | 200 | 7.1 |
|  |  | 400 | 12.6 |
|  |  | 700 | 26 |
|  |  | 1000 | 32 |

Examples 3-4

These Examples demonstrate that the membrane-permeation test of the present invention can be used to evaluate the effectiveness of a pharmaceutical composition in enhancing the concentration of drug in solution.

For Example 3, the pharmaceutical composition consisted of a solid amorphous dispersion of 25 wt % Drug 1 in the "M" grade of hydroxypropyl methyl cellulose acetate succinate (AQOAT-MG available from Shin Etsu, Tokyo, Japan, referred to herein as HPMCAS-M) formed by spray drying as follows. First, a spray solution was formed containing 25 g Drug 1, 75 g HPMCAS-MG, and 900 g acetone. The spray solution was pumped using a high-pressure pump (Zenith Z-Drive 2000 High-Pressure Gear Pump) to a spray drier (Niro type XP Portable Spray-Dryer with a Liquid-Feed Process Vessel [PSD-1]) equipped with a pressure atomizer (Spraying Systems Pressure Nozzle and Body (SK 79-16)). The PSD-1 was equipped with a 9-inch chamber extension. The spray drier was also equipped with a diffuser plate having a 1% open area. The nozzle sat flush with the diffuser plate during operation. The spray solution was pumped to the spray drier at about 185 gm/min, with an atomization pressure of about 280 psig. Drying gas (nitrogen) was circulated through the diffuser plate at an inlet temperature of about 98° C. The evaporated solvent and wet drying gas exited the spray drier at a temperature of about 31° C. The spray-dried dispersion formed by this process was collected in a cyclone, and was post-dried using a Gruenberg single-pass convection tray dryer operating at 40° C. for about 16 hours. Details on the spray drying process for forming the solid amorphous dispersion are included in U.S. patent application Ser. No. 09/918,127, which published as U.S. Patent Application Publication No. 20020103225, incorporated herein by reference. For Example 4, the pharmaceutical composition consisted of crystalline Drug 1 alone.

To evaluate the pharmaceutical compositions of Examples 3 and 4, a permeate reservoir was formed as described in Example 1. This permeate reservoir was used in a membrane-permeation test apparatus similar to the one shown in FIG. 4 and FIG. 5. The apparatus was placed onto a magnetic stir plate to stir the feed and permeate solutions at 100 rpm.

The organic fluid used in these tests consisted of 5 mL of 20 wt % decanol in decane. Tests showed that the solubility of Drug 1 in this organic fluid was about 25 mg/mL. Thus, the partition coefficient of the drug between the organic fluid and water was greater than about 650,000.

Figure 10:
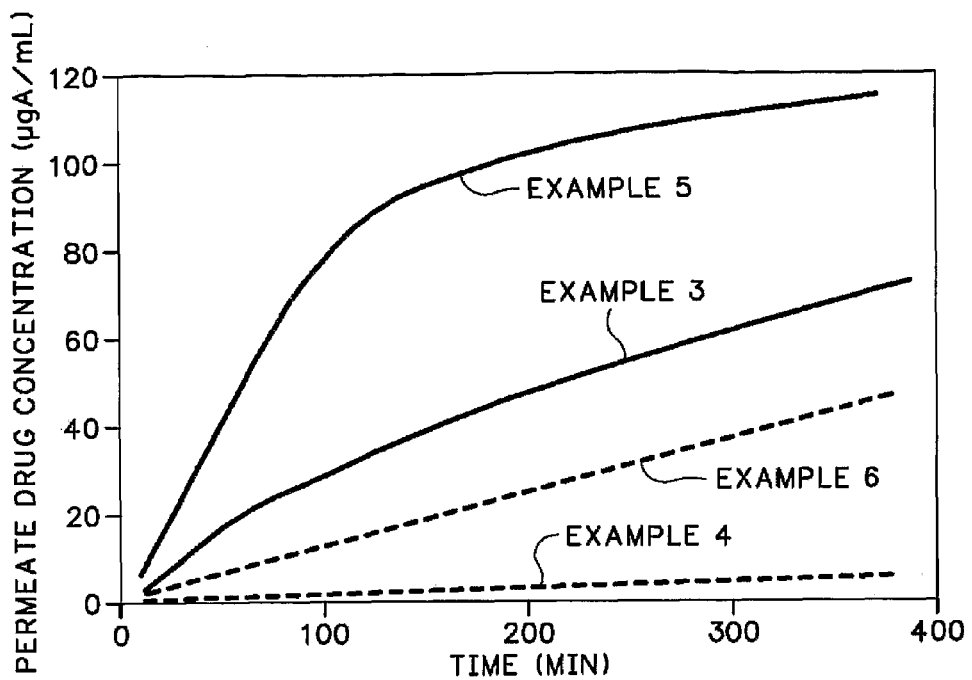
FIG. 10 shows the permeate concentration versus time for the membrane-permeation tests of Examples 3-6.

The feed solutions were formed by placing the pharmaceutical composition into 5 mL of MFD solution consisting of PBS containing 7.3 mM sodium taurocholic acid and 1.4 mM of 1-palmitoyl-2-oleyl-sn-glycero-3-phosphocholine. A sufficient quantity of the pharmaceutical composition was added to the MFD solution so that the concentration of drug would have been 120 μg/mL if all of the drug had dissolved. The mixtures were placed on a vortex mixer for 30 seconds prior to beginning the test. Samples were taken at prescribed time intervals, and the concentration of Drug 1 in the permeate solution was determined as described in Example 1 with the exception that 50-μL samples were collected and diluted 1:6 with isopropyl alcohol (IPA). FIG. 10 shows the concentration of drug versus time obtained from these tests. From these data the maximum flux of drug across the membrane was determined using the procedures described in Example 1. The results are summarized in Table 5, and show that the maximum flux of the solid amorphous dispersion of Example 3 was 28-fold that of the crystalline Drug 1 of Example 4. Without wishing to be bound by any particular theory or mechanism of action, it is believed the higher maximum flux provided by the composition of Example 3 relative to crystalline drug was due to at least two factors. First, it is believed the solid amorphous dispersion of Example 3 provides an enhanced dissolved drug concentration for Drug 1. As indicated by Equation 3, a higher dissolved drug concentration leads to a higher maximum flux. It is believed that the higher dissolved drug concentration provided by the dispersion of Example 3 also results in a proportionally higher concentration of drug in bile-salt micelles present in the MFD feed solution, leading to an increase in transport of drug through the unstirred water layer. The combination of these two factors results in the increased maximum flux of Drug 1.

TABLE 5

| Example | Composition | Test Media | Maximum Flux of Drug 1 (μg/cm²-min) |
|---|---|---|---|
| 3 | 25% Drug 1: HPMCAS-M Dispersion | MFD | 0.34 |
| 4 | Crystalline Drug 1 | MFD | 0.012 |

Examples 5-6

These examples demonstrate that the membrane permeation test of the present invention can be used to estimate the effects of food on the in vivo performance of a pharmaceutical composition.

For Example 5, the pharmaceutical composition was a solid amorphous dispersion of Drug 1 as described for Example 3. For Example 6, the pharmaceutical composition was crystalline Drug 1. Membrane permeation tests were performed as described for Examples 3 and 4, except that the pharmaceutical compositions were added to 5 mL of a solution to model the fed state, consisting of PBS containing 29.2 mM sodium taurocholic acid and 5.6 mM of 1-palmitoyl-2-oleyl-sn-glycero-3-phosphocholine. The results of these tests are shown in FIG. 10, and summarized in Table 6, along with the results for Examples 3 and 4 tested in MFD solution, which models the fasted state, for comparison. These data show that the maximum flux for the solid amorphous dispersion of Example 5 when added to a solution modeling the fed state was 2,6-fold the maximum flux when tested in MFD state. Additionally, the maximum flux for crystalline drug when added to a solution modeling the fed state was 7,6-fold the maximum flux when tested in MFD solution. These data suggest that in vivo, the bioavailability of Drug 1 will be higher in the fed state than in the fasted state. Without wishing to be bound by any particular theory or mechanism of action, it is believed that the higher maximum flux obtained when tested in a solution modeling the fed state relative to the maximum flux for the MFD solution (Example 3) was due to a higher concentration of bile-salt micelles, and therefore, more drug in bile-salt micelles. A higher concentration of drug in bile-salt micelles results in a higher value of $P_{micelles}$, and therefore, a higher value of $P_{ov}$. This higher value of $P_{ov}$ in turn, results in a higher rate of transport of drug through the unstirred water layer, which in turn, results in an increase in the overall transport rate even though the concentration of dissolved drug was the same. As shown by Equation 3, a higher overall permeability coefficient will result in a higher maximum flux even if the concentration of dissolved drug ($[D_{dissolved}]$) is the same.

TABLE 6

| Example | Composition | Test Media | Maximum Flux of Drug 1 (μg/cm²-min) |
|---|---|---|---|
| 3 | 25% Drug 1: HPMCAS-M Dispersion | MFD (fasted state) | 0.34 |
| 5 | 25% Drug 1: HPMCAS-M Dispersion | Solution to Model the Fed State | 0.87 |
| 4 | Crystalline Drug 1 | MFD (fasted state) | 0.012 |
| 6 | Crystalline Drug 1 | Solution to Model the Fed State | 0.091 |

Examples 7-10

The compositions tested in vitro in Examples 3-6 were tested in vivo to determine whether the in vitro results correlate with the in vivo results. For Examples 7 and 8, the composition was the same as that used in Example 3 (25% Drug 1:HPMCAS-M dispersion) dosed in the fasted state, and fed state, respectively. For Examples 9 and 10, the composition was the same as that used in Example 4 (crystalline Drug 1) dosed in the fasted state and fed state, respectively.

The compositions were orally dosed to beagle dogs in the form of an oral powder for constitution (OPC) by suspending the composition in about 15 mL of a solution of 3 wt % polyethylene glycol (PEG) with a molecular weight of 3,350 daltons, 0.5 wt % methylcellulose, and 0.15 wt % Polysorbate 80 in sterile water. In each case a sufficient amount of the pharmaceutical composition was used such that the OPC contained 90 mgA of Drug 1. The thus-formed OPCs were then dosed to dogs in either the fed state or fasted state (fasted overnight). Blood was collected from the jugular vein of the dogs before dosing and at various time points after dosing. To 100 μL of each plasma sample, 5 mL of methyl-tert-butyl ether (MTBE) and 1 mL of 500 mM sodium carbonate buffer (pH 9) were added; the sample was vortexed for 1 minute and then centrifuged for 5 minutes. The aqueous portion of the sample was frozen in a dry-ice/acetone bath, and the MTBE layer was decanted and evaporated in a vortex evaporator. Dried samples were reconstituted in 100 μL of mobile phase (33% acetonitrile and 67% of 0.1% formic acid in water). Analysis was carried out by HPLC.

The results of these tests are shown in Table 7, where $C_{max,24}$ is the maximum concentration in the blood plasma during the first 24 hours, $T_{max}$ is the time to achieve the maximum concentration in the blood plasma and $AUC_{0-24}$ is the concentration in the blood plasma area under the curve in the first 24 hours.

TABLE 7

| Example | Composition | Fed or Fasted State | $C_{max,24}$ (μg/mL) | $T_{max}$ (hr) | $AUC_{0-24}$ (μg-hr/mL) |
|---|---|---|---|---|---|
| 7 | 25% Drug 1: HPMCAS-M Dispersion (Example 3 composition) | Fasted | 485 ± 217 | 1.3 ± 0.9 | 1959 ± 1175 |
| 8 | 25% Drug 1: HPMCAS-M Dispersion (Example 3 composition) | Fed | 1281 ± 610 | 1.0 ± 0.1 | 6673 ± 1255 |
| 9 | Crystalline Drug 1 (Example 4 composition) | Fasted | ND* | ND | ND |
| 10 | Crystalline Drug 1 (Example 4 composition) | Fed | 191 ± 55 | 2.3 ± 1.9 | 928 ± 642 |

*ND = not detected

These data show that Drug 1 provided a higher systemic concentration of Drug 1 (e.g., a higher $C_{max,24}$) and a higher bioavailability (e.g., a higher $AUC_{0-24}$) in the fed state than in the fasted state, confirming the results of the membrane-permeation tests. Specifically, the solid amorphous dispersion of Drug 1 provided a $C_{max,24}$ in the fed state (Example 8) that was 2,6-fold that in the fasted state (Example 7), and an $AUC_{0-24}$ in the fed state (Example 8) that was 3,4-fold that in the fasted state (Example 7). This is in excellent agreement with the in vitro membrane permeation test results in which the dispersion provided a maximum flux in a solution used to model the fed state that was 2,6-fold the maximum flux obtained using a solution modeling the fasted state. The data also show that the solid amorphous dispersion (Examples 7 and 8) provided a higher systemic concentration and bioavailability than crystalline Drug 1 (Examples 9 and 10), confirming the results of the in vitro membrane-permeation tests.

Example 11

This example demonstrates that the membrane-permeation test can be used to evaluate a pharmaceutical composition consisting of a drug adsorbed to a solid substrate. Membrane permeation tests were performed using the apparatus and methods described in Examples 3 and 4 with the following exceptions. The pharmaceutical composition comprised 25 wt % Drug 1 adsorbed to CAB-O-SIL M-5P (fumed silica from Cabot Corporation, Midland, Mich.) as a solid substrate (surface area of about 200 m²/gm). The drug/substrate adsorbate was formed using a solvent process where the solvent (acetone) was rapidly removed using a spray drying process as follows. First, CAB-O-SIL M-5P was added to acetone and then sonicated using a Fisher Scientific SF15 sonicator for 10 minutes to ensure full suspension and homogeneity. Drug 1 was then dissolved in this suspension resulting in a mixture that contained 0.56 wt % Drug 1, 1.68 wt % CAB-O-SIL M-5P, and 97.8 wt % acetone. This suspension was then pumped into a "mini" spray-drying apparatus via a Cole Parmer 74900 series rate-controlling syringe pump at a rate of about 1.2 mL/min. The spray-drying apparatus used a Spraying Systems Co. two-fluid nozzle, model number SU1A, with nitrogen as the atomizing gas. The nitrogen was pressurized and heated to a temperature of 100° C. and had a flow rate of about 1 SCFM. The suspension was sprayed from the top of an 11-cm diameter stainless steel chamber. The resulting solid amorphous adsorbate was collected on Whatman® 1 filter paper at a yield of about 46%, dried under vacuum, and stored in a desiccator. Further details of the process for forming the drug/substrate adsorbate are provided in commonly-assigned, pending U.S. patent application Ser. No. 10/173, 987, which published as U.S. Patent Application Publication No. 20030054037, the disclosure of which is incorporated herein by reference.

The feed solution was formed by adding a sufficient quantity of the drug/substrate adsorbate to 5 mL of MFD solution so that the Drug 1 concentration if all of the drug had dissolved would have been 120 μg/mL. The permeate solution consisted of 5 mL of 20 wt % decanol in decane. Samples of the permeate solution were collected over time and analyzed for Drug 1 concentrations as described in Examples 3 and 4. From these data, the maximum flux of Drug 1 across the membrane was calculated as described in Examples 1 and 2. The results are summarized in Table 8, which includes the results for Example 4 for comparison. These data show that the drug/substrate adsorbate of Example 11 provided a maximum flux that was almost 27-fold that provided by crystalline Drug 1, demonstrating that the pharmaceutical composition of Example 11 provides enhanced concentrations of Drug 1. As previously discussed for other compositions, this higher maximum flux is believed to be caused by the higher dissolved drug concentration provided by the composition of Example 11, as well as the resulting increased concentration of drug in bile-salt micelles, which leads to an increased overall permeability coefficient.

TABLE 8

| Example | Composition | Test Media | Maximum Flux of Drug 1 (μg/cm²-min) |
|---|---|---|---|
| 11 | 25% Drug 1: CAB-O-SIL Adsorbate | MFD | 0.32 |
| 4 | Crystalline Drug 1 | MFD | 0.012 |

Examples 12-15

These Examples demonstrate the effectiveness of the membrane-permeation test for evaluating pharmaceutical compositions containing the glycogen phosphorylase inhibitor (GPI) 5-chloro-1H-indole-2-carboxylic acid [(1S)-benzyl-(2R)-hydroxy-3-((3R,4S)-dihydroxy-pyrrolidin-1-yl-)-3-oxypropyl]amide ("Drug 2"). Drug 2 has an aqueous solubility of about 80 μg/mL. For Example 12, the pharmaceutical composition consisted of crystalline Drug 2. For Examples 13-15, the pharmaceutical composition consisted of a solid amorphous dispersion of 50 wt % Drug 2 in HPMCAS-M, which was made by a spray drying process similar to that described for Example 3. In each case, the feed solution was formed by placing a sufficient quantity of the pharmaceutical composition into 5 mL of the test media so that the concentration of Drug 2 would have been 2000 μg/mL if all of the drug had dissolved. Table 9 lists the test media used in these tests.

For Examples 12-15, the organic fluid used was 60 wt % decanol in decane. The solubility of Drug 2 in this mixture was determined to be about 940 μg/mL. Thus, the partition coefficient of Drug 2 between the organic fluid and water was about 12.

Membrane permeation tests were performed using the apparatus and procedures outlined in Examples 3 and 4 with the following exceptions. Samples of the permeate were collected at the prescribed times and diluted 1:6 with IPA. Drug 2 concentrations were analyzed via UV absorbance at a wavelength of 297 nm. From the concentration versus time data the maximum flux of Drug 2 across the membrane was determined as described in Examples 1 and 2. The results are summarized in Table 9. These data show that the solid amorphous dispersion of Example 13 provided a maximum flux of Drug 2 that was 5,3-fold that provided by crystalline Drug 2 (Example 12). This increase in maximum flux is believed to be a result of the higher dissolved drug concentration provided by the solid amorphous dispersion of Example 13 compared to crystalline Drug 2.

The results also show that adding bile-salt micelles to the test media results in a decrease in the maximum flux of Drug 2. When bile-salt micelles are added to the feed solution, a portion of the drug will partition into the bile-salt micelles. It is believed that for Example 14, a sufficient amount of drug partitioned into bile-salt micelles such that the concentration of dissolved drug decreased relative to the test performed without bile-salt micelles (Example 13). As a result, although drug in bile-salt micelles can lead to an increase in the rate of transport of drug through the unstirred water layer, and therefore an increase in the overall permeability coefficient, the decrease in dissolved drug concentration resulted in a lower maximum flux for Drug 2. The data also show that adding more bile-salt micelles to the feed (Example 15) further reduces the maximum flux, likely due to a further reduction in the dissolved drug concentration.

These data suggest that Drug 2 will have a lower bioavailability in the fed state than in the fasted state. This conclusion is in agreement with in vivo tests with Drug 2.

TABLE 9

| Example | Composition | Test Media | Maximum Flux of Drug 2 (μg/cm$^2$-min) |
|---|---|---|---|
| 12 | Crystalline Drug 2 | PBS | 3.7 |
| 13 | 50 Wt % Drug 2: HPMCAS-M Dispersion | PBS | 19.5 |
| 14 | 50 wt % Drug 2: HPMCAS-M Dispersion | MFD (fasted state) | 17.2 |
| 15 | 50 wt % Drug 2: HPMCAS-M Dispersion | Solution to Model the Fed State | 7.9 |

Examples 16-17

These Examples demonstrate the effectiveness of the membrane-permeation test for evaluating pharmaceutical compositions containing the CETP inhibitor [2R,4S]4-[acetyl-(3,5-bis-trifluoromethyl-benzyl)-amino]-2-ethyl-6-trifluoromethyl-3,4-dihydro-2H-quinoline-1-carboxylic acid isopropyl ester ("Drug 3"). Drug 3 has an aqueous solubility of less than 0.1 μg/mL. For Example 16, the pharmaceutical composition consisted of crystalline Drug 3. For Example 17, the pharmaceutical composition consisted of a solid amorphous dispersion of 25 wt % Drug 3 in HPMCAS-M, which was made by a spray drying process similar to that described for Example 3. In each case, the feed solution was formed by placing a sufficient quantity of the pharmaceutical composition into 5 mL of MFD solution so that the concentration of Drug 3 would have been 120 μg/mL if all of the drug had dissolved.

For Examples 16-17, the organic fluid used was 20 wt % decanol in decane. The solubility of Drug 3 in this mixture was determined to be greater than about 25 mg/mL. Thus, the partition coefficient of Drug 3 between the organic fluid and water is greater than 250,000.

Membrane permeation tests were performed using the apparatus and procedures outlined in Examples 3 and 4 with the following exceptions. Samples of the permeate were collected at the prescribed times and diluted 1:6 with IPA. Drug 3 concentrations were analyzed via HPLC at a UV absorbance of 256 nm using the procedures outlined in Example 1. From the concentration versus time data the maximum flux of Drug 3 across the membrane was determined as described in Examples 1 and 2. The results are summarized in Table 10. These data show that the solid amorphous dispersion of Example 17 provided a maximum flux that was 7,7-fold that provided by crystalline Drug 3 (Example 16). As previously discussed for other compositions, this higher maximum flux is believed to be caused by the higher dissolved drug concentration provided by the composition of Example 17, as well as the resulting increased concentration of drug in bile-salt micelles, which leads to an increased overall permeability coefficient.

TABLE 10

| Example | Composition | Test Media | Maximum Flux of Drug 3 (μg/cm$^2$-min) |
|---|---|---|---|
| 16 | Crystalline Drug 3 | MFD | 0.06 |
| 17 | 25 wt % Drug 3: HPMCAS-M Dispersion | MFD | 0.46 |

Example 18

This example demonstrates the use of a permeate reservoir formed by heat sealing a membrane to a polyethylene tube and using a UV probe for analyzing the concentration of drug in the permeate.

A permeate reservoir was formed by heat-sealing a sample of the plasma-treated membrane previously described to a polyethylene tube having an inside diameter of about 1 inch (2.54 cm). The feed side of the membrane was oriented so that it was on the outside of the permeate reservoir, while the permeate-side of the membrane was oriented so that it was on the inside of the reservoir.

This permeate reservoir was then used in an apparatus similar to the one described for Examples 3 and 4. The pharmaceutical composition was a solid amorphous dispersion of 25 wt % Drug 1 in HPMCAS-M, as described for Example 3. The feed solution was prepared by placing a sufficient quantity of the dispersion into 5 mL of MFD solution so that the concentration of drug would have been 120 µg/mL if all of the drug had dissolved. The organic solution consisted of 5 mL of 20 wt % decanol in decane.

The test was performed using the procedures outlined in Examples 3 and 4 with the following exceptions. The concentration of drug in the permeate solution was determined by placing a UV probe in the permeate solution and monitoring absorbance over time and converting to concentration using standards. The UV probe had a 5-mm path length and was obtained from C Technologies, Inc. (Cedar Hills, N.J.). The probes were attached to a Cassini Multiplexer (from C Technologies) that was installed on a Cary 50 Bio UV/Vis Spectrophotometer by Varian, Inc. (Walnut Creek, Calif.). The UV probe system was programmed to measure the absorbance at 256 nm every 2 minutes for the first 30 minutes, every 10 minutes up to 360 minutes, and every 60 minutes up to 2880 minutes.

Figure 11:
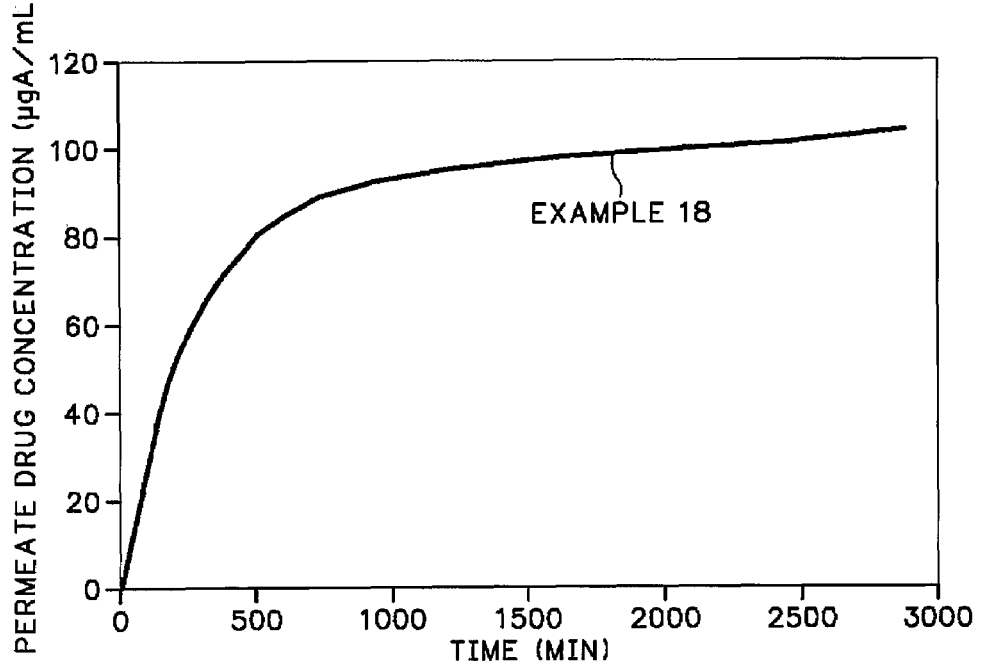
FIG. 11 shows the permeate concentration versus time for the membrane-permeation test of Example 14.

FIG. 11 shows the results of the test. From these data the maximum flux was calculated to be 0.28 µg/cm$^2$-min.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

The invention claimed is:

1. A method for evaluating a pharmaceutical composition comprising a drug, said method comprising:
    (1) providing a microporous membrane having a plurality of pores, said membrane being made from a hydrophobic material, and said membrane having a hydrophilic feed side and a permeate side, wherein said feed side of said membrane is in fluid communication with a feed solution, and wherein said permeate side of said membrane is in fluid communication with a permeate solution;
    (2) administering said pharmaceutical composition to an aqueous solution to form said feed solution; and
    (3) measuring the concentration of said drug in said permeate solution;
    wherein said permeate side of said microporous membrane has a contact angle for a drop of water of greater than about 90° and said feed side of said microporous membrane has a contact angle for a drop of water of less than about 70°, and wherein said permeate solution comprises an organic fluid that is substantially immiscible with water.

2. The method of claim 1 wherein said pores have a nominal size of about 0.02 µm to about 0.5 µm.

3. The method of claim 1 wherein said drug has a partition coefficient between said organic fluid and water of at least 5.

4. The method of claim 1 wherein said organic fluid is selected from the group consisting of alkanes, alkenes, alcohols, ethers, ketones, aromatics, alkyl halides, and mixtures thereof.

5. The method of claim 1 wherein said organic fluid comprises a mixture of at least one alkane having from 8 to 12 carbon atoms and at least one alcohol having from 8 to 12 carbon atoms.

6. The method of claim 1 wherein said aqueous solution is selected from the group consisting of phosphate buffered saline, simulated intestinal buffer without enzymes, a model fasted duodenal solution, and a solution to model the fed state.

7. The method of claim 1 wherein said drug is a low-solubility drug.

* * * * *